United States Patent
Dubois et al.

(10) Patent No.: US 8,153,796 B2
(45) Date of Patent: Apr. 10, 2012

(54) TRICYCLIC N-HETEROARYL-CARBOXAMIDE DERIVATIVES, PREPARATION AND THERAPEUTIC USE THEREOF

(75) Inventors: Laurent Dubois, Paris (FR); Yannick Evanno, Paris (FR); Andre Malanda, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/696,149

(22) Filed: Jan. 29, 2010

(65) Prior Publication Data

US 2010/0173929 A1  Jul. 8, 2010

Related U.S. Application Data

(63) Continuation of application No. PCT/FR2008/001141, filed on Jul. 31, 2008.

(30) Foreign Application Priority Data

Aug. 2, 2007 (FR) ...................................... 07 05677

(51) Int. Cl.
- A61K 31/4375 (2006.01)
- C07D 471/14 (2006.01)
- A61P 29/00 (2006.01)
- A61P 13/00 (2006.01)
- A61P 31/22 (2006.01)
- A61P 25/24 (2006.01)

(52) U.S. Cl. .......................................... 546/82; 514/293

(58) Field of Classification Search .................. None
See application file for complete search history.

(56) References Cited

U.S. PATENT DOCUMENTS 6,313,242 B1 * 11/2001 Reddy ........................... 526/160

FOREIGN PATENT DOCUMENTS

| WO | WO 2004/072069 | 8/2004 |
| WO | WO 2004/108133 | 12/2004 |
| WO | WO 2005/016922 | 2/2005 |

OTHER PUBLICATIONS

Antilla, J. C., et. al.,, The Copper-Catalyzed N-Arylation of Indoles, J. Am. Chem. Soc., vol. 124, No. 39, (2002), pp. 11684-11688.
Crampton, M. R., et. al., Kinetic and Equilibrium Studies of a-Adduct Formation and Nucleophilic Substitution in the Reactions of 2-Phenoxy-3,5-Dinitropyridine and 2-Exthoxy-3,5-Dinitropyridine with Aliphatic Amines in Dipolar Aprotic Solvents, Org. Biomol. Chem., (2003), vol. 1, pp. 1004-1011.
Furstner, A., et. al., Iron-Catalyzed Cross-Coupling Reactions, J. Am Chem Soc., (2002), vol. 124, pp. 13856-13863.
Klapars, A. et. al., A General and Efficient Copper Catalyst for the Amidation of Aryl Halides and the N-Arylation of Nitrogen Heterocycles, J. Am. Chem. Soc., (2001) pp. 7727-7729 vol. 123.
Kyle. D. J., et. al., TRPV1 Antagonists: A Survey of the Patent Literature, Expert Opinion on Therapeutic Patents. vol. 16, No. 7, pp. 977-996, (2006).
Trecourt, F., et. al., First Syntheses of Caerulomycin E and Collismycins A and C. A New Synthesis of Caerulomycin A. J. Org. Chem., (1998), vol. 63, pp. 2892-2897.
Williams, T. M., et. al., 5-Chloro-3-(Phenylsulfonyl)Indole-2-Carboxamide: A Novel, Non-Nucleoside Inhibitor of HIV-1 Reverse Transcriptase, J. Med. Chem., (1993), vol. 36, pp. 1291-1294.

* cited by examiner

*Primary Examiner* — Brandon Fetterolf
*Assistant Examiner* — Dennis Heyer
(74) *Attorney, Agent, or Firm* — Scully, Scott, Murphy & Presser, P.C.

(57) ABSTRACT

The invention relates to tricyclic N-heteroaryl-carboxamide derivatives having the formula (I):

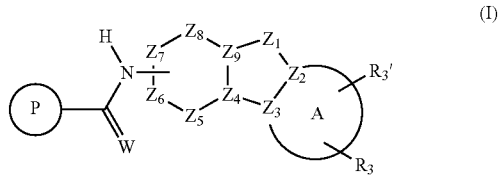

Wherein A, P, W, $Z_1$, $Z_2$, $Z_3$, $Z_4$, $Z_5$, $Z_6$, $Z_7$, $Z_8$, $R_3$ and $R_3'$ are as described herein. The invention also relates to a method for preparing the same and to the therapeutic use thereof.

14 Claims, No Drawings

TRICYCLIC N-HETEROARYL-CARBOXAMIDE DERIVATIVES, PREPARATION AND THERAPEUTIC USE THEREOF

This application is a continuation of International application No. PCT/FR2008/001,141, filed Jul. 31, 2008, which is incorporated herein by reference in its entirety; which claims the benefit of priority of French patent application Ser. No. 07/05,677, filed Aug. 2, 2007.

Documents WO2006/024776, WO2006/072736, WO2007/010144 and WO2007/010138 describe bicyclic N-heteroarylcarboxamide derivatives which exhibit antagonist activity in vitro and in vivo for TRPV1 (or VR1) receptors.

There is still a need to find new antagonists for TRPV1 receptors.

The present invention meets this need by providing tricyclic N-heteroarylcarboxamide derivatives which exhibit antagonist activity in vitro and in vivo for TRPV1 (or VR1) receptors.

The invention first provides the compounds conforming to the general formula (I) below.

The invention further provides processes for preparing compounds of general formula (I).

The invention further provides for the use of the compounds of general formula (I) more particularly in medicaments or in pharmaceutical compositions.

The compounds of the invention conform to general formula (I):

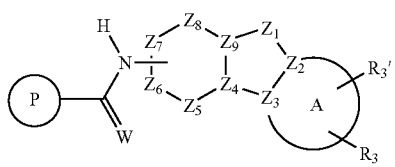

in which:

A, together with the $Z_2$—$Z_3$ bond of the bicyclic system to which it is fused, represents a $C_4$-$C_7$-cycloalkyl group, a monocyclic heteroaryl or a monocyclic heterocycle of 4 to 7 members, including from one to three heteroatoms selected from O, S and N, including the atoms $Z_2$ and $Z_3$;

$Z_1$, $Z_5$, $Z_6$, $Z_7$ and $Z_8$ represent, independently of one another, a nitrogen atom, a carbon atom or a group C—$R_2$;

$Z_2$, $Z_3$, $Z_4$ and $Z_9$ represent, independently of one another, a nitrogen atom or a carbon atom and $Z_1$, $Z_2$, $Z_3$, $Z_4$, $Z_5$, $Z_6$, $Z_7$, $Z_8$ and $Z_9$ together form a bicyclic heteroaryl bonded to the nitrogen atom of the amide or thioamide of formula (I) via the positions $Z_5$, $Z_6$, $Z_7$ or $Z_8$ when these positions correspond to a carbon atom, with one at least of $Z_4$, $Z_5$, $Z_6$, $Z_7$, $Z_8$ and $Z_9$ corresponding to a nitrogen atom;

W represents an oxygen or sulfur atom;

P represents an indolyl, pyrrolo[2,3-c]pyridinyl, pyrrolo[2,3-b]pyridinyl, pyrrolo[3,2-b]pyridinyl or pyrrolo[3,2-c]pyridinyl group as shown below, bonded at position C-2 to the carbonyl of the amide or to the thiocarbonyl of the thioamide of formula (I):

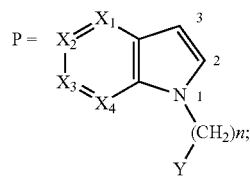

$X_1$, $X_2$, $X_3$ and $X_4$ represent, independently of one another, a nitrogen atom or a group C—$R_1$; when one of $X_1$, $X_2$, $X_3$ or $X_4$ represents a nitrogen atom, the three others represent a group C—$R_1$;

$R_1$ is selected from a hydrogen atom, a halogen atom, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl-$C_1$-$C_3$-alkylenoxy-$C_1$-$C_6$-alkyl, arylthio-$C_1$-$C_6$-alkyl, heteroarylthio-$C_1$-$C_6$-alkyl, aryl-$C_1$-$C_3$-alkylenethio-$C_1$-$C_6$-alkyl, heteroaryl-$C_1$-$C_3$-alkylenethio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)N$R_4R_5$, nitro, N$R_4R_5$, $C_1$-$C_6$-thioalkyl, $C_3$-$C_7$-cycloalkylthio, $C_3$-$C_7$-cycloalkyl-$C_1$-$C_3$-alkylenethio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, SO$_2$N$R_4R_5$, SF$_5$, N$R_6$C(O)$R_7$, N$R_6$SO$_2R_8$, C(O)N$R_4R_5$, OC(O)N$R_4R_5$, aryl, heteroaryl, aryl-$C_1$-$C_5$-alkylene, heteroaryl-$C_1$-$C_5$-alkylene, aryloxy, arylthio, heteroaryloxy or heteroarylthio, the heteroaryl or aryl groups being optionally substituted by one or more substituents $R_9$, which are identical or different from one another;

n is 0, 1, 2 or 3;

Y represents an aryl or a heteroaryl which is optionally substituted by one or more groups selected from a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxy, $C_1$-$C_6$-alkoxy, $C_3$-$C_7$-cycloalkyloxy, $C_3$-$C_7$-cycloalkyl-$C_1$-$C_6$-alkylene-O—, $C_1$-$C_6$-fluoroalkoxy, cyano, C(O)N$R_4R_5$, nitro, N$R_4R_5$, $C_1$-$C_6$-thioalkyl, thiol, —S(O)—$C_1$-$C_6$-alkyl, —S(O)$_2$—$C_1$-$C_6$-alkyl, SO$_2$N$R_4R_5$, N$R_6$C(O)$R_7$, N$R_6$SO$_2R_8$, C(O)N$R_4R_5$, OC(O)N$R_4R_5$, aryl-$C_1$-$C_5$-alkylene or aryl, heteroaryl-$C_1$-$C_5$-alkylene or heteroaryl group, the aryl and heteroaryl groups being optionally substituted by one or more substituents selected from a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano group;

$R_2$ represents a hydrogen atom, a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, thiol, —S(O)—$C_1$-$C_6$-alkyl, —S(O)$_2$—$C_1$-$C_6$-alkyl, hydroxyl or $C_1$-$C_6$-fluoroalkoxy group;

$R_3$ and $R_3'$ represent the substituents of A with the exclusion of the substituents of the atoms $Z_2$ and $Z_3$;

$R_3$ and $R_3'$ represent, independently of one another, when they are carried by a carbon atom, a hydrogen atom, a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, thiol, $C_1$-$C_6$-alkoxy, $C_3$-$C_7$-cycloalkyloxy, $C_3$-$C_7$-cycloalkyl-$C_1$-$C_3$-alkylenoxy, aryl-C(O)—O—, $C_1$-$C_6$-alkyl-C(O)—O—, $C_3$-$C_7$-cycloalkyl-C(O)—O—, $C_3$-$C_7$-cycloalkyl-$C_1$-$C_3$-alkylene-C(O)—O, $C_1$-$C_6$-fluoroalkyl-C(O)—O—, oxo, thiol, $NR_4R_5$, $NR_6C(O)R_7$, heteroaryl or aryl group, the heteroaryl and aryl groups being optionally substituted by one or more substituents selected from a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano group;

or else $R_3$ and $R_3'$, together with the carbon atom which carries them, form a $C_3$-$C_7$-cycloalk-1,1-diyl group;

or $R_3$ and $R_3'$ represent, independently of one another, when they are carried by a nitrogen atom, a hydrogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, aryl-S(O)—, $C_1$-$C_6$-alkyl-S(O)—, $C_1$-$C_6$-fluoroalkyl-S(O)—, $C_3$-$C_7$-cycloalkyl-S(O)—, $C_3$-$C_7$-cycloalkyl-$C_1$-$C_3$-alkylene-S(O)—, aryl-S(O)$_2$—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, $C_1$-$C_6$-alkyl-O—C(O)—, aryl-$C_1$-$C_3$-alkyl-O—C(O)—, $C_3$-$C_7$-cycloalkyl-O—C(O)—, $C_3$-$C_7$-cycloalkyl-$C_1$-$C_3$-alkylene-O—C(O)—, $C_1$-$C_6$-fluoroalkyl-O—C(O)—, aryl-O—C(O)—, heteroaryl-O—C(O)—, heteroaryl or aryl group, the heteroaryl and aryl groups being optionally substituted by one or more substituents selected from a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano group;

$R_4$ and $R_5$ represent, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl group, or $R_4$ and $R_5$, together with the nitrogen atom which carries them, form an azetidine, pyrrolidine, piperidine, azepine, morpholine, thiomorpholine, piperazine or homopiperazine group, the group $NR_4R_5$ being optionally substituted by a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$, $C_3$-$C_7$-cycloalkyl-S(O)$_2$—, $C_3$-$C_7$-cycloalkyl-$C_1$-$C_3$-alkylene-S(O)$_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxy, $C_1$-$C_6$-alkyloxy, $C_3$-$C_7$-cycloalkyloxy, $C_3$-$C_7$-cycloalkyl-$C_1$-$C_3$-alkylenoxy, $C_1$-$C_6$-fluoroalkyl, aryloxy-$C_1$-$C_6$-alkylene, aryloxy, heteroaryloxy-$C_1$-$C_6$-alkylene or heteroaryloxy group;

$R_6$ and $R_7$ represent, independently of one another, a hydrogen atom, a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group, the aryl group being optionally substituted by one or more substituents selected from a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano group;

or $R_6$ and $R_7$ together form a lactam of 4 to 7 members comprising the nitrogen atom and the group C(O) which carry them;

$R_8$ represents a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group, the aryl group being optionally substituted by one or more substituents selected from a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano group;

or $R_6$ and $R_8$ together form a sultam of 4 to 7 members, comprising the nitrogen atom and the group S(O)$_2$ which carry them;

$R_9$ represents a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro, cyano, $NR_4R_5$ or $R_4R_5N$—$C_1$-$C_3$-alkylene group.

In the compounds of general formula (I):

the sulfur atom or atoms of the heterocycle A may be in oxidized form (S(O) or S(O)$_2$);

the nitrogen atom or atoms may optionally be in oxidized form (N-oxide).

The compounds of formula (I) may contain one or more asymmetric carbon atoms.

They may therefore exist in the form of enantiomers or diastereoisomers. These enantiomers and diastereoisomers, and also mixtures thereof, including the racemic mixtures, form part of the invention.

The compounds of formula (I) may exist in the form of bases or addition salts with acids. Such addition salts form part of the invention.

These salts may be prepared with pharmaceutically acceptable acids, although the salts of other acids that can be used, for example, for purifying or isolating compounds of formula (I) also form part of the invention.

The compounds of formula (I) may also exist in the form of hydrates or solvates, i.e. in the form of associations or combinations with one or more molecules of water or with a solvent. Such hydrates and solvates also form part of the invention.

In the context of the present invention the terms below have the following meanings:

a halogen atom: a fluorine, a chlorine, a bromine or an iodine;

$C_t$-$C_z$: a carbon chain that can have from t to z carbon atoms, where t and z may have the values from 1 to 7; for example, $C_1$-$C_3$ is a carbon chain that may have from 1 to 3 carbon atoms;

an alkyl: a linear or branched, saturated aliphatic group. Examples include the groups methyl, ethyl, propyl, isopropyl, butyl, isobutyl, tert-butyl, pentyl, etc;

an alkylene: a linear or branched, saturated divalent alkyl group; for example, a $C_{1-3}$-alkylene group represents a divalent carbon chain of 1 to 3 carbon atoms which is linear or branched, more particularly a methylene, ethylene, 1-methylethylene or propylene;

a cycloalkyl: a saturated or partially unsaturated cyclic alkyl group. Examples include the groups cyclopropyl, cyclobutyl, cyclopentyl, cyclohexyl, etc;

a cycloalk-1,1-diyl: a group of the type

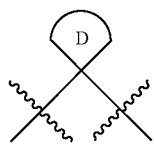

in which D represents a cycloalkyl group;

a fluoroalkyl: an alkyl group one or more of whose hydrogen atoms have been substituted by a fluorine atom;

an alkoxy: an —O-alkyl radical where the alkyl group is as defined above;

a fluoroalkoxy: an alkoxy group one or more of whose hydrogen atoms have been substituted by a fluorine atom;

a thioalkyl or alkylthio: an —S-alkyl radical where the alkyl group is as defined above;

an aryl: a monocyclic or bicyclic aromatic group containing between 6 and 10 carbon atoms. Examples of aryl groups include the groups phenyl or naphthyl;

a heterocycle: a saturated or partially unsaturated monocyclic group, of 4 to 8 members, containing from 1 to 5 heteroatoms selected from O, S and N.

Examples of heterocycles include the groups azetidinyl, pyrrolidinyl, piperidinyl, azepinyl, morpholinyl, thiomorpholinyl, piperazinyl, homopiperazinyl, dihydrooxazolyl, dihydrothiazolyl, dihydroimidazolyl, dihydropyrrolyl or tetrahydropyridinyl, tetrahydro[1,2]oxazine tetrahydro[1,3]oxazine, tetrahydro[1,4]oxazine, [1,3]oxazepine or [1,4]oxazepine.

a heteroaryl: a monocyclic or bicyclic aromatic group of 5 to 12 members, containing from 1 to 5 heteroatoms selected from O, S and N.

Examples of monocyclic heteroaryl include the groups imidazolyl, pyrazolyl, thiazolyl, oxazolyl, isothiazolyl, isoxazolyl, furanyl, thiophenyl, oxadiazolyl, thiadiazolyl, triazolyl, tetrazolyl, pyridinyl, pyrazinyl, pyrimidinyl, pyridazinyl and triazinyl.

Examples of bicyclic heteroaryl include the groups indolyl, isoindolyl, benzofuranyl, benzothiophenyl, benzoxazolyl, benzimidazolyl, indazolyl, benzothiazolyl, isobenzofuranyl, isobenzothiazolyl, pyrrolo[2,3-c]pyridinyl, pyrrolo[2,3-b]pyridinyl, pyrrolo[3,2-b]pyridinyl, pyrrolo[3,2-c]pyridinyl, pyrrolo[1,2-a]pyridinyl, quinolinyl, isoquinolinyl, cinnolinyl, quinazolinyl, quinoxalinyl, pyrrolo[1,2-a]imidazolyl, imidazo[1,2-a]pyridinyl, imidazo[1,2-a]pyridazinyl, imidazo[1,2-c]pyrimidinyl, imidazo[1,2-a]pyrimidinyl, imidazo[1,2-a]pyrazinyl, imidazo[4,5-b]pyrazinyl, imidazo[4,5-b]pyridinyl, imidazo[4,5-c]pyridinyl, pyrazolo[2,3-a]pyridinyl, pyrazolo[2,3-a]pyrimidinyl, pyrazolo[2,3-a]pyrazinyl.

"oxo" signifies "=O";

"thio" signifies "=S".

Among the compounds of general formula (I) a first group of compounds is composed of the compounds which conform to the general formula (Ia):

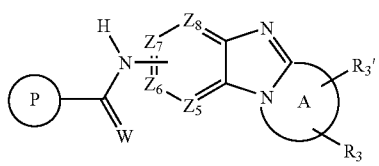

(Ia)

A, $Z_5$, $Z_6$, $Z_7$, $Z_8$, P, W, $R_3$ and $R_3'$ being as defined in the general formula (I).

Among the compounds of general formula (I), a second group of compounds is composed of the compounds which conform to the general formula (Ib):

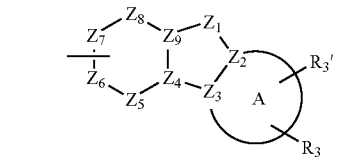

(Ib)

$Z_6$, $Z_7$ and $Z_8$ represent, independently of one another, a carbon atom or a group C—$R_2$; one of $Z_6$, $Z_7$ or $Z_8$ corresponds to a carbon atom and is bonded to the nitrogen atom of the amide or thioamide of formula (Ib);

A, P, W, $R_2$, $R_3$ and $R_3'$ are as defined in the general formula (I).

Among the compounds of general formula (I), a third group of compounds is composed of the compounds of general formula (I) for which the group

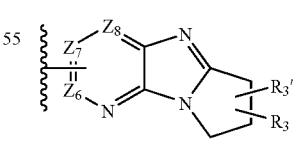

is selected from:

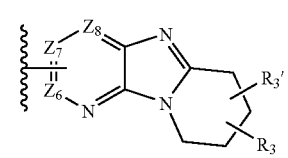

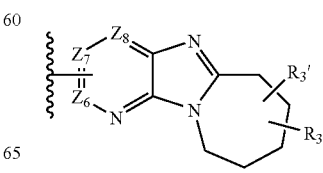

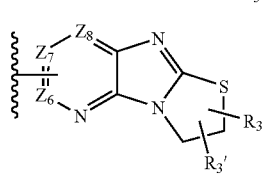

-continued

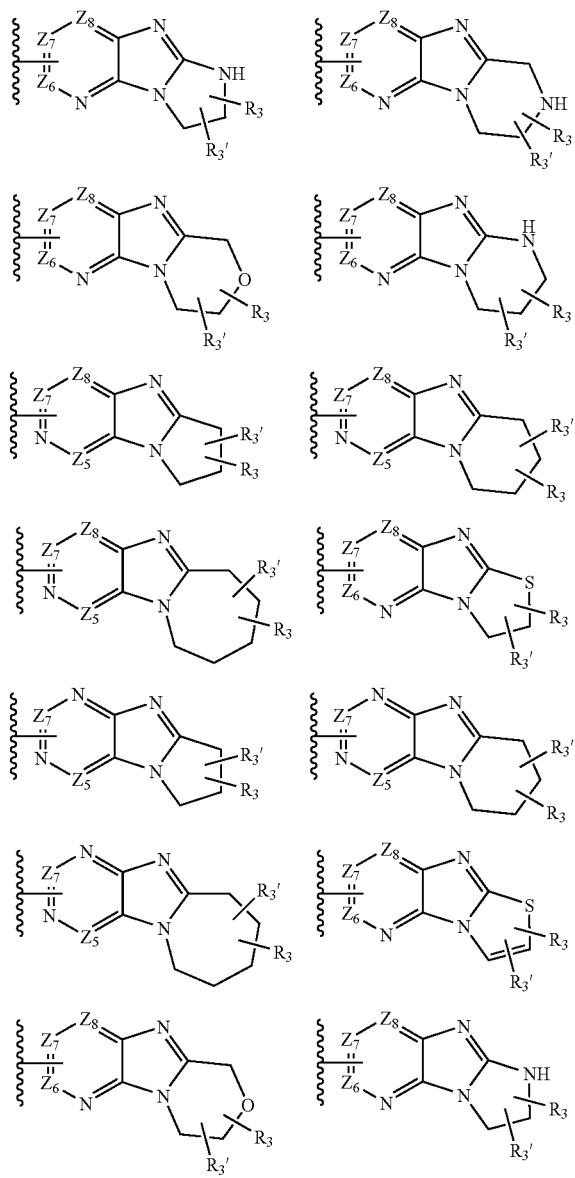

$Z_5$, $Z_6$, $Z_7$ and $Z_8$ represent, independently of one another, a carbon atom bonded to the nitrogen atom of the amide or thioamide of formula (I), or a group C—$R_2$;

$R_2$, $R_3$ and $R_3'$ are as defined in the general formula (I).

Among the compounds of general formula (I), a fourth group of compounds is composed of the compounds of general formula (I) for which $R_2$ represents a hydrogen atom;

$R_3$ and $R_3'$ are carried by a carbon atom and represent, independently of one another, a hydrogen atom, a halogen atom, or a $C_1$-$C_6$-alkyl, hydroxyl, $C_1$-$C_6$-alkyl-C(O)—O—, $NR_4R_5$, $NR_6C(O)R_7$ or aryl group;

$R_4$ and $R_5$ represent, independently of one another, a hydrogen atom or a $C_1$-$C_6$-alkyl group;

$R_6$ and $R_7$ represent, independently of one another, a hydrogen atom or a $C_1$-$C_6$-alkyl group.

Among the compounds of general formula (I), a fifth group of compounds is composed of the compounds of general formula (I) for which
the group

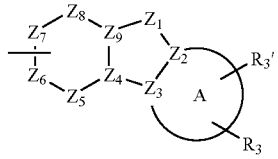

is selected from:

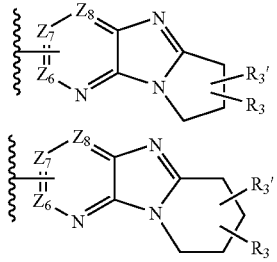

$Z_6$, $Z_7$ and $Z_8$ represent, independently of one another, a carbon atom bonded to the nitrogen atom of the amide or thioamide of formula (I), or a group C—$R_2$;

$R_2$ represents a hydrogen atom;

$R_3$ and $R_3'$ are carried by a carbon atom and represent, independently of one another, a hydrogen atom, a halogen atom or a $C_1$-$C_6$-alkyl, hydroxyl, $C_1$-$C_6$-alkyl-C(O)—O—, $NR_4R_5$, $NR_6C(O)R_7$ or aryl group;

$R_4$ and $R_5$ represent, independently of one another, a hydrogen atom or a $C_1$-$C_6$-alkyl group;

$R_6$ and $R_7$ represent, independently of one another, a hydrogen atom or a $C_1$-$C_6$-alkyl group.

Among the compounds of general formula (I), a sixth group of compounds is composed of the compounds of general formula (I) for which W represents an oxygen atom.

Among the compounds of general formula (I), a seventh group of compounds is composed of the compounds of general formula (I) for which
P represents an indolyl or pyrrolo[2,3-b]pyridinyl group as shown below, bonded in position C-2 to the carbonyl of the amide or to the thiocarbonyl of the thioamide of formula (I):

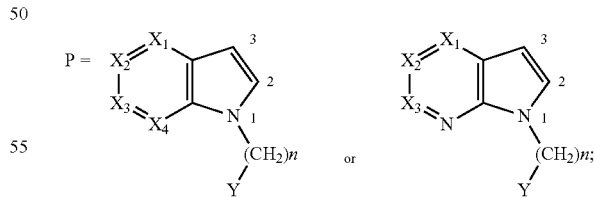

$X_1$, $X_2$, $X_3$ and $X_4$ represent, independently of one another, a group C—$R_1$;

$R_1$, Y and n are as defined in the general formula (I).

Among the compounds of general formula (I), an eighth group of compounds is composed of the compounds of general formula (I) for which $R_1$ is selected from a hydrogen atom, a halogen atom, $C_1$-$C_6$-alkyl, $C_1$-$C_6$-fluoroalkyl, $C_1$-$C_6$-thioalkyl and $C_1$-$C_6$-alkyl-S(O)$_2$—.

Among the compounds of general formula (I), a ninth group of compounds is composed of the compounds of general formula (I) for which n is 1.

Among the compounds of general formula (I), a tenth group of compounds is composed of the compounds of general formula (I) for which Y represents an aryl, more particularly a phenyl, which is optionally substituted by one or more halogen atoms, more particularly fluorine atoms.

Among the compounds of general formula (I), an eleventh group of compounds is composed of the compounds of general formula (I) for which
P represents an indolyl or pyrrolo[2,3-b]pyridinyl group as shown below, bonded in position C-2 to the carbonyl of the amide or to the thiocarbonyl of the thioamide of formula (I):

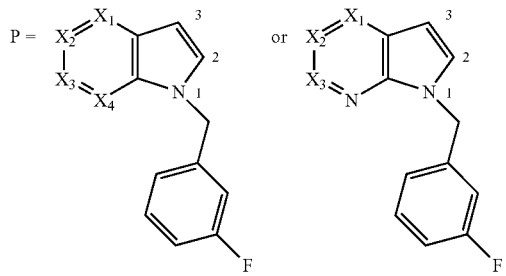

$X_1$, $X_2$, $X_3$ and $X_4$ represent, independently of one another, a group C—$R_1$;
$R_1$ is selected from a hydrogen atom, a halogen atom, $C_1$-$C_6$-alkyl, $C_1$-$C_6$-fluoroalkyl, $C_1$-$C_6$-thioalkyl and $C_1$-$C_6$-alkyl-S($O)_2$—.

Among the compounds of general formula (I), a twelfth group of compounds is composed of the compounds of general formula (I) for which
the group

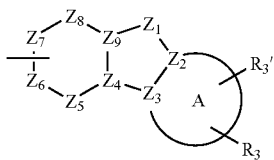

is selected from:

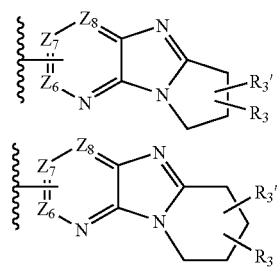

$Z_6$, $Z_7$ and 4 represent, independently of one another, a carbon atom bonded to the nitrogen atom of the amide or thioamide of formula (I), or a group C—$R_2$;
$R_2$ represents a hydrogen atom;
$R_3$ and $R_3'$ are carried by a carbon atom and represent, independently of one another, a hydrogen atom, a halogen atom or a $C_1$-$C_6$-alkyl, hydroxyl, $C_1$-$C_6$-alkyl-C(O)—O—, $NR_4R_5$, $NR_6C(O)R_7$ or aryl group;

$R_4$ and $R_5$ represent, independently of one another, a hydrogen atom or a $C_1$-$C_6$-alkyl group;
$R_6$ and $R_7$ represent, independently of one another, a hydrogen atom or a $C_1$-$C_6$-alkyl group;
W represents an oxygen atom;
P represents an indolyl or pyrrolo[2,3-b]pyridinyl group as shown below, bonded in position C-2 to the carbonyl of the amide or to the thiocarbonyl of the thioamide of formula (I):

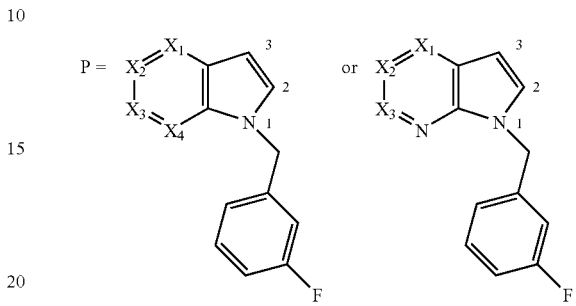

$X_1$, $X_2$, $X_3$ and $X_4$ represent, independently of one another, a group C—$R_1$;
$R_1$ is selected from a hydrogen atom, a halogen atom, $C_1$-$C_6$-alkyl, $C_1$-$C_6$-fluoroalkyl, $C_1$-$C_6$-thioalkyl and $C_1$-$C_6$-alkyl-S($O)_2$—.

Among the compounds of general formula (I), a thirteenth group of compounds is composed of the compounds of general formula (I) in which simultaneously P and/or W and/or $Z_1$ and/or $Z_2$ and/or $Z_3$ and/or $Z_4$ and/or $Z_5$ and/or $Z_6$ and/or $Z_7$ and/or $Z_8$ and/or $Z_9$ and/or A and/or $R_3$ and/or $R_3'$ are as defined in the groups defined above.

Among the compounds of general formula (I) that are subject matter of the invention, mention may be made in particular of the following compounds:

N-(2,3-dihydro-1H-pyrrolo[1',2':1,2]imidazo[5,4-b]pyridin-6-yl)-5-fluoro-1-(3-fluorobenzyl)-1H-indole-2-carboxamide N-(3-acetoxy-2,3-dihydro-1H-pyrrolo[1',2':1,2]imidazo[5,4-b]pyridin-6-yl)-5-fluoro-1-(3-fluorobenzyl)-1H-indole-2-carboxamide N-(2,3-dihydro-3-hydroxy-1H-pyrrolo[1',2':1,2]imidazo[5,4-b]pyridin-6-yl)-5-fluoro-1-(3-fluorobenzyl)-1H-indole-2-carboxamide N-(2,3-dihydro-3-oxo-1H-pyrrolo[1',2':1,2]imidazo[5,4-b]pyridin-6-yl)-5-fluoro-1-(3-fluorobenzyl)-1H-indole-2-carboxamide (1,2,3,4-tetrahydropyrido[1',2':1,2]imidazo[5,4-b]pyridin-7-yl)-5-fluoro-1-(3-fluorobenzyl)-1H-indole-2-carboxamide (1,2-dihydro-4H-oxazino[1,4][4',3':1,2]imidazo[5,4-b]pyridin-7-yl)-5-fluoro-1-(3-fluorobenzyl)-1H-indole-2-carboxamide (1,2,3,4-tetrahydro-2-methylpyrazino[4',3':1,2]imidazo[5,4-b]pyridin-7-yl)-5-fluoro-1-(3-fluorobenzyl)-1H-indole-2-carboxamide (3,4-dihydro-2-oxo-1H-pyrazino[4',3':1,2]imidazo[5,4-b]pyridin-7-yl)-5-fluoro-1-(3-fluorobenzyl)-1H-indole-2-carboxamide (1,2-dihydro-3-oxo-4H-pyrimido[1',2'1,2]imidazo[5,4-b]pyridin-7-yl)-5-fluoro-1-(3-fluorobenzyl)-1H-indole-2-carboxamide (1,2-dihydro-4-oxo-3H-pyrazino[4',3':1,2]imidazo[5,4-b]pyridin-7-yl)-5-fluoro-1(3-fluorobenzyl)-1H-indole-2-carboxamide N-(2,3-dihydro-3-dimethylamino-1H-pyrrolo[1',2',1,2]imidazo[5,4-b]pyridin-6-yl)-5-fluoro-1-(3-fluorobenzyl)-1H-indole-2-carboxamide N-(2,3-dihydro-3-phenyl-1H-pyrrolo[1',2':1,2]imidazo[5,4-b]pyridin-6-yl)-5-fluoro-1-(3-fluorobenzyl)-1H-indole-2-carboxamide N-(2,3-dihydro-1-phenyl-1H-pyrrolo[1',2:1,2]imidazo[5,4-b]pyridin-6-yl)-5-fluoro-1-(3-fluorobenzyl)-1H-indole-2-carboxamide N-[2,3-dihydro-1-(pyridin-3-yl)-1H-pyrrolo[1',2:1,2]imidazo[5,4-b]pyridin-6-yl]-5-fluoro-1-(3-fluorobenzyl)-1H-indole-2-carboxamide N-(2,3-dihydro-2-hydroxy-1-methyl-1H-pyrrolo[1',2:1,2]imidazo[5,4-b]pyridin-6-yl)-5-fluoro-1-(3-fluorobenzyl)-1H-indole-2-carboxamide N-(2,3-dihydro-1H-pyrrolo[1',2:1,2]imidazo[4,5-b]pyrazin-6-yl)-5-fluoro-1-(3-fluorobenzyl)-1H-indole-2-carboxamide N-(2,3-dihydro-1H-pyrrolo[1',2':1,2]imidazo[4,5-b]pyridin-6-yl)-5-fluoro-1-(3-fluorobenzyl)-1H-indole-2-carboxamide N-(2,3-dihydro-1H-pyrrolo[1',2':1,2]imidazo[5,4-c]pyridin-6-yl)-5-fluoro-1-(3-fluorobenzyl)-1H-indole-2-carboxamide N-(2,3-dihydro-1H-cyclopenta[4,5]imidazo[1,2-a]pyridin-6-yl)-5-fluoro-1-(3-fluorobenzyl)-1H-indole-2-carboxamide N-(2,3-dihydro-1H-cyclopenta[4,5]imidazo[1,2-b]pyridazin-6-yl)-5-fluoro-1-(3-fluorobenzyl)-1H-indole-2-carboxamide N-(2,3-dihydro-1H-cyclopenta[4,5]imidazo[1,2-a]pyrimidin-6-yl)-5-fluoro-1-(3-fluorobenzyl)-1H-indole-2-carboxamide N-(2,3-dihydro-1H-cyclopenta[4,5]pyrazolo[2,3-a]pyridin-7-yl)-5-fluoro-1-(3-fluorobenzyl)-1H-indole-2-carboxamide N-(2,3-dihydro-1H-cyclopenta[4,5]pyrazolo[2,3-a]pyrimidin-7-yl)-5-fluoro-1-(3-fluorobenzyl)-1H-indole-2-carboxamide N-(2,3-dihydro-1H-cyclopenta[4,5]pyrazolo[2,3-a]pyrazin-7-yl)-5-fluoro-1-(3-fluorobenzyl)-1H-indole-2-carboxamide N-(2,3-dihydro-1H-pyrrolo[1',2':1,2]imidazo[5,4-b]pyridin-6-yl)-4-fluoro-1-(3-fluorobenzyl)-1H-indole-2-carboxamide N-(2,3-dihydro-1H-pyrrolo[1',2':1,2]imidazo[5,4-b]pyridin-6-yl)-6-fluoro-1-(3-fluorobenzyl)-1H-indole-2-carboxamide N-(2,3-dihydro-1H-pyrrolo[1',2':1,2]imidazo[5,4-b]pyridin-6-yl)-7-fluoro-1-(3-fluorobenzyl)-1H-indole-2-carboxamide N-(2,3-dihydro-1H-pyrrolo[1',2':1,2]imidazo[5,4-b]pyridin-6-yl)-6-trifluoromethyl-1-(3-fluorobenzyl)-1H-indole-2-carboxamide N-(2,3-dihydro-1H-pyrrolo[1',2':1,2]imidazo[5,4-b]pyridin-6-yl)-5-trifluoromethyl-1-(3-fluorobenzyl)-1H-indole-2-carboxamide N-(2,3-dihydro-1H-pyrrolo[1',2':1,2]imidazo[5,4-b]pyridin-6-yl)-4-chloro-1-(3-fluorobenzyl)-1H-indole-2-carboxamide N-(2,3-dihydro-1H-pyrrolo[1',2':1,2]imidazo[5,4-b]pyridin-6-yl)-6-chloro-1-(3-fluorobenzyl)-1H-indole-2-carboxamide N-(2,3-dihydro-1H-pyrrolo[1',2':1,2]imidazo[5,4-b]pyridin-6-yl)-5-chloro-1-(3-fluorobenzyl)-1H-indole-2-carboxamide N-(2,3-dihydro-1H-pyrrolo[1',2':1,2]imidazo[5,4-b]pyridin-6-yl)-1-(3-fluorobenzyl)-1H-indole-2-carboxamide N-(2,3-dihydro-1H-pyrrolo[1',2':1,2]imidazo[5,4-b]pyridin-6-yl)-4-methyl-1-(3-fluorobenzyl)-1H-indole-2-carboxamide N-(2,3-dihydro-1H-pyrrolo[1',2':1,2]imidazo[5,4-b]pyridin-6-yl)-6-methyl-1-(3-fluorobenzyl)-1H-indole-2-carboxamide N-(2,3-dihydro-1H-pyrrolo[1',2':1,2]imidazo[5,4-b]pyridin-6-yl)-5-methyl-1-(3-fluorobenzyl)-1H-indole-2-carboxamide N-(2,3-dihydro-1H-pyrrolo[1',2':1,2]imidazo[5,4-b]pyridin-6-yl)-6-ethyl-1-(3-fluorobenzyl)-1H-indole-2-carboxamide N-(2,3-dihydro-1H-pyrrolo[1',2':1,2]imidazo[5,4-b]pyridin-6-yl)-5-isopropyl-1-(3-fluorobenzyl)-1H-indole-2-carboxamide N-(2,3-dihydro-1H-pyrrolo[1',2':1,2]imidazo[5,4-b]pyridin-6-yl)-6-isopropyl-1-(3-fluorobenzyl)-1H-indole-2-carboxamide N-(2,3-dihydro-1H-pyrrolo[1',2':1,2]imidazo[5,4-b]pyridin-6-yl)-5-tertbutyl-1-(3-fluorobenzyl)-1H-indole-2-carboxamide N-(2,3-dihydro-1H-pyrrolo[1',2':1,2]imidazo[5,4-b]pyridin-6-yl)-6-tertbutyl-1-(3-fluorobenzyl)-1H-indole-2-carboxamide N-(2,3-dihydro-1H-pyrrolo[1',2':1,2]imidazo[5,4-b]pyridin-6-yl)-4,7-dimethyl-1-(3-fluorobenzyl)-1H-indole-2-carboxamide N-(2,3-dihydro-1H-pyrrolo[1',2':1,2]imidazo[5,4-b]pyridin-6-yl)-5-methylsulfonyl-1-(3-fluorobenzyl)-1H-indole-2-carboxamide N-(2,3-dihydro-1H-pyrrolo[1',2':1,2]imidazo[5,4-b]pyridin-6-yl)-6-methylthio-1-(3-fluorobenzyl)-1H-indole-2-carboxamide N-(2,3-dihydro-1H-pyrrolo[1',2':1,2]imidazo[5,4-b]pyridin-6-yl)-5-fluoro-1-[(4-pyridyl)methyl]-1H-indole-2-carboxamide N-(2,3-dihydro-1H-pyrrolo[1',2':1,2]imidazo[5,4-b]pyridin-6-yl)-5-trifluoromethyl-1-[(4-pyridyl)methyl]-1H-pyrrolo[2,3-b]pyridine-2-carboxamide N-(2,3-dihydro-1H-pyrrolo[1',2':1,2]imidazo[5,4-b]pyridin-6-yl)-5-trifluoromethyl-1-(3-fluorobenzyl)-1H-pyrrolo[2,3-b]pyridine-2-carboxamide N-(2,3-dihydro-1H-pyrrolo[1',2':1,2]imidazo[5,4-b]pyridin-6-yl)-6-trifluoromethyl-1-(3-fluorobenzyl)-1H-pyrrolo[2,3-b]pyridine-2-carboxamide N-(2,3-dihydro-1H-pyrrolo[1',2':1,2]imidazo[5,4-b]pyridin-6-yl)-5-fluoro-1-(3-fluorobenzyl)-1H-pyrrolo[2,3-b]pyridine-2-carboxamide N-(2,3-dihydro-1H-pyrrolo[1',2':1,2]imidazo[5,4-b]pyridin-6-yl)-5-trifluoromethyl-1-(3-fluorobenzyl)-1H-pyrrolo[3,2-b]pyridine-2-carboxamide Among the compounds of general formula (I) that are subject matter of the invention, mention may be made in particular of the following compounds:

N-(7,8-Dihydro-6H-pyrrolo[2',1':2,3]imidazo[4,5-b]pyridin-3-yl)-5-fluoro-1-(3-fluorobenzyl)-1H-indole-2-carboxamide N-(6-Acetoxy-7,8-dihydro-6H-pyrrolo[2',1':2,3]imidazo[4,5-b]pyridin-3-yl)-5-fluoro-1-(3-fluorobenzyl)-1H-indole-2-carboxamide N-(6-Hydroxy-7,8-dihydro-6H-pyrrolo[2',1':2,3]imidazo[4,5-b]pyridin-3-yl)-5-fluoro-1-(3-fluorobenzyl)-1H-indole-2-carboxamide N-(7,8-Dihydro-6H-pyrrolo[2',1':2,3]imidazo[4,5-b]pyridin-3-yl)-4-fluoro-1-(3-fluorobenzyl)-1H-indole-2-carboxamide N-(7,8-Dihydro-6H-pyrrolo[2',1':2,3]imidazo[4,5-b]pyridin-3-yl)-7-fluoro-1-(3-fluorobenzyl)-1H-indole-2-carboxamide N-(7,8-Dihydro-6H-pyrrolo[2',1':2,3]imidazo[4,5-b]pyridin-3-yl)-6-fluoro-1-(3-fluorobenzyl)-1H-indole-2-carboxamide N-(7,8-Dihydro-6H-pyrrolo[2',1':2,3]imidazo[4,5-b]pyridin-3-yl)-6-trifluoromethyl-1-(3-fluorobenzyl)-1H-indole-2-carboxamide N-(7,8-Dihydro-6H-pyrrolo[2',1':2,3]imidazo[4,5-b]pyridin-3-yl)-5-trifluoromethyl-1-(3-fluorobenzyl)-1H-indole-2-carboxamide N-(7,8-Dihydro-6H-pyrrolo[2',1':2,3]imidazo[4,5-b]pyridin-3-yl)-4-chloro-1-(3-fluorobenzyl)-1H-indole-2-carboxamide N-(7,8-Dihydro-6H-pyrrolo[2',1':2,3]imidazo[4,5-b]pyridin-3-yl)-6-chloro-1-(3-fluorobenzyl)-1H-indole-2-carboxamide N-(7,8-Dihydro-6H-pyrrolo[2',1':2,3]imidazo[4,5-b]pyridin-3-yl)-5-chloro-1-(3-fluorobenzyl)-1H-indole-2-carboxamide N-(7,8-Dihydro-6H-pyrrolo[2',1':2,3]imidazo[4,5-b]pyridin-3-yl)-1-(3-fluorobenzyl)-1H-indole-2-carboxamide N-(7,8-Dihydro-6H-pyrrolo[2',1':2,3]imidazo[4,5-b]pyridin-3-yl)-4-methyl-1-(3-fluorobenzyl)-1H-indole-2-carboxamide N-(7,8-Dihydro-6H-pyrrolo[2',1':2,3]imidazo[4,5-b]pyridin-3-yl)-6-methyl-1-(3-fluorobenzyl)-1H-indole-2-carboxamide N-(7,8-Dihydro-6H-pyrrolo[2',1':2,3]imidazo[4,5-b]pyridin-3-yl)-5-methyl-1-(3-fluorobenzyl)-1H-indole-2-carboxamide N-(7,8-Dihydro-6H-pyrrolo[2',1':2,3]imidazo[4,5-b]pyridin-3-yl)-6-ethyl-1-(3-fluorobenzyl)-1H-indole-2-carboxamide N-(7,8-Dihydro-6H-pyrrolo[2',1':2,3]imidazo[4,5-b]pyridin-3-yl)-6-isopropyl-1-(3-fluorobenzyl)-1H-indole-2-carboxamide N-(7,8-Dihydro-6H-pyrrolo[2',1':2,3]imidazo[4,5-b]pyridin-3-yl)-5-tertbutyl-1-(3-fluorobenzyl)-1H-indole-2-carboxamide N-(7,8-Dihydro-6H-pyrrolo[2',1':2,3]imidazo[4,5-b]pyridin-3-yl)-6-tertbutyl-1-(3-fluorobenzyl)-1H-indole-2-carboxamide N-(7,8-Dihydro-6H-pyrrolo[2',1':2,3]imidazo[4,5-b]pyridin-3-yl)-4,7-dimethyl-1-(3-fluorobenzyl)-1H-indole-2-carboxamide N-(7,8-Dihydro-6H-pyrrolo[2',1':2,3]imidazo[4,5-b]pyridin-3-yl)-5-methylsulfonyl-1-(3-fluorobenzyl)-1H-indole-2-carboxamide N-(7,8-Dihydro-6H-pyrrolo[2',1':2,3]imidazo[4,5-b]pyridin-3-yl)-6-methylthio-1-(3-fluorobenzyl)-1H-indole-2-carboxamide N-(7,8-Dihydro-6H-pyrrolo[2',1':2,3]imidazo[4,5-b]pyridin-3-yl)-6-trifluoromethyl-1-(3-fluorobenzyl)-1H-pyrrolo[2,3-b]pyridine-2-carboxamide N-(7,8-Dihydro-6H-pyrrolo[2',1':2,3]imidazo[4,5-b]pyridin-3-yl)-5-trifluoromethyl-1-(3-fluorobenzyl)-1H-pyrrolo[2,3-b]pyridine-2-carboxamide N-(7,8-Dihydro-6H-pyrrolo[2',1':2,3]imidazo[4,5-b]pyridin-3-yl)-5-fluoro-1-(3-fluorobenzyl)-1H-pyrrolo[2,3-b]pyridine-2-carboxamide N-(6-Hydroxy-7,8-dihydro-6H-pyrrolo[2',1':2,3]imidazo[4,5-b]pyridin-3-yl)-5-trifluoromethyl-1-(3-fluorobenzyl)-1H-indole-2-carboxamide N-(6,7,8,9-tetrahydroimidazo[1,2-a:5,4-b']dipyridin-3-yl)-5-trifluoromethyl-1-(3-fluorobenzyl)-1H-indole-2-carboxamide (−)-N-(6-Hydroxy-7,8-dihydro-6H-pyrrolo[2',1':2,3]imidazo[4,5-b]pyridin-3-yl)-6-trifluoromethyl-1-(3-fluorobenzyl)-1H-indole-2-carboxamide N-(6-Phenyl-7,8-dihydro-6H-pyrrolo[2',1':2,3]imidazo[4,5-b]pyridin-3-yl)-5-trifluoromethyl-1-(3-fluorobenzyl)-1H-indole-2-carboxamide N-(6,6-Dimethyl-7,8-dihydro-6H-pyrrolo[2',1':2,3]imidazo[4,5-b]pyridin-3-yl)-5-trifluoromethyl-1-(3-fluorobenzyl)-1H-indole-2-carboxamide (−)-N-(6-Dimethylamino-7,8-dihydro-6H-pyrrolo[2',1':2,3]imidazo[4,5-b]pyridin-3-yl)-5-trifluoromethyl-1-(3-fluorobenzyl)-1H-indole-2-carboxamide N-(6-amino-7,8-dihydro-6H-pyrrolo[2',1':2,3]imidazo[4,5-b]pyridin-3-yl)-5-fluoro-1-(3-fluorobenzyl)-1H-indole-2-carboxamide N-(6-Acetylamino-7,8-dihydro-6H-pyrrolo[2',1':2,3]imidazo[4,5-b]pyridin-3-yl)-5-fluoro-1-(3-fluorobenzyl)-1H-indole-2-carboxamide (−)-N-(6-Hydroxy-7,8-dihydro-6H-pyrrolo[2',1':2,3]imidazo[4,5-b]pyridin-3-yl)-5-trifluoromethyl-1-(3-fluorobenzyl)-1H-pyrrolo[2,3-b]pyridine-2-carboxamide (+)-N-(6-Fluoro-7,8-dihydro-6H-pyrrolo[2',1':2,3]imidazo[4,5-b]pyridin-3-yl)-6-trifluoromethyl-1-(3-fluorobenzyl)-1H-indole-2-carboxamide N-(6-Amino-7,8-dihydro-6H-pyrrolo[2',1':2,3]imidazo[4,5-b]pyridin-3-yl)-5-trifluoromethyl-1-(3-fluorobenzyl)-1H-indole-2-carboxamide A leaving group in the text below means a group that can be readily cleaved from a molecule by the breaking of a heterolytic bond, with the departure of an electron pair. This group can thus be readily replaced by another group in a substitution reaction, for example. Leaving groups of this kind are, for example, halogens or an activated hydroxyl group such as a methanesulfonate, benzenesulfonate, p-toluenesulfonate, triflate, acetate, etc. Examples of leaving groups and also references for their preparation are given in "Advances in Organic Chemistry", J. March, 5th Edition, Wiley Interscience, 2001.

A protective group in the text below means a group that can be momentarily incorporated into a chemical structure with the aim of temporarily inactivating a part of the molecule during a reaction, and that may readily be removed at a later step in the synthesis. Examples of protective groups and also references concerning their properties are given in T. W. Greene, P. G. M. Wutz, 3rd Edition, Wiley Interscience 1999.

In accordance with the invention, the compounds of general formula (I) can be prepared by the process illustrated by the general Scheme 1 below:

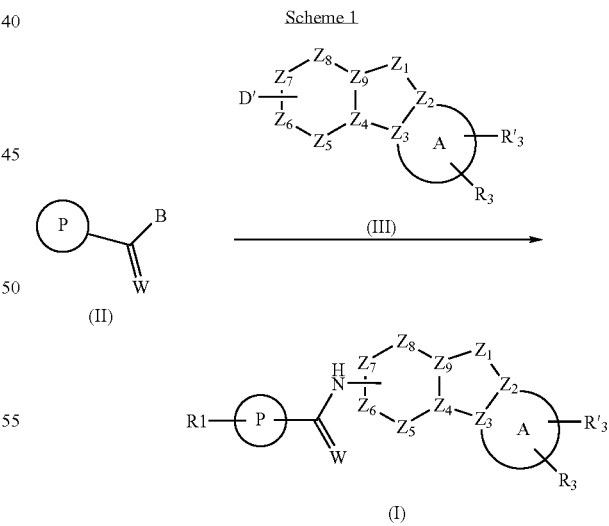

The compounds (I) can be obtained by reaction of a compound of general formula (II) in which B represents a $C_1$-$C_6$-alkoxy, $C_3$-$C_7$-cycloalkyloxy, $C_3$-$C_7$-cycloalkyl-$C_1$-$C_3$-alkylenoxy or aryl-$C_1$-$C_3$-alkylenoxy group, and W and P are as defined in the general formula (I), with a compound of general formula (III) in which D' represents an amide group and A, $Z_1$, $Z_2$, $Z_3$, $Z_4$, $Z_5$, $Z_6$, $Z_7$, $Z_8$, $Z_9$, $R_3$ and $R_3'$ are as defined in the general formula (I) above, under the reflux of a solvent such as toluene. The aluminum amide of the compound of general formula (III) may be prepared by the prior action of trimethylaluminum on the amines of general formula (III) in which D' represents an $NH_2$ group.

Starting from compounds of general formula (II) in which B represents a hydroxyl group, W represents an oxygen atom and P is as defined in the general formula (I), the carboxylic acid function may be converted beforehand to acid halide such as an acid chloride by the action, for example, of thionyl chloride, under reflux of a solvent such as dichloromethane or dichloroethane. The compound of general formula (I) can then be obtained by reaction of compounds of general formula (II) in which B represents a chlorine atom, W represents an oxygen atom and P is as defined in the general formula (I) with the compound of general formula (III) in which A, $Z_1$, $Z_2$, $Z_3$, $Z_4$, $Z_5$, $Z_6$, $Z_7$, $Z_8$, $Z_9$, $R_3$ and $R_3'$ are as defined in the general formula (I) above and D' represents an $NH_2$ group, in the presence of a base such as triethylamine or sodium carbonate. Alternatively the compounds of general formula (II) in which B represents a hydroxyl group, W represents an oxygen atom and P is as defined in the general formula (I) may be coupled with the compounds of general formula (III) in which A, $Z_1$, $Z_2$, $Z_3$, $Z_4$, $Z_5$, $Z_6$, $Z_7$, $Z_8$, $Z_9$, $R_3$ and $R_3'$ are as defined in the general formula (I) above and D' represents an $NH_2$ group, in the presence of a coupling agent such as dialkylcarbodiimide, [(benzotriazol-1-yl)oxy][tris(pyrrolidino)]phosphonium hexafluorophosphate, diethyl cyanophosphonate or any other coupling agent known to the skilled person, in the presence of a base such as triethylamine, in a solvent such as, for example, dimethylformamide.

Starting from compounds of general formula (II) in which B represents an $NH_2$ group, W represents an oxygen atom and P is as defined in the general formula (I), the compound of general formula (I) may be obtained by reaction with the compound of general formula (III) in which A, $Z_1$, $Z_2$, $Z_3$, $Z_4$, $Z_5$, $Z_6$, $Z_7$, $Z_8$, $Z_9$, $R_3$ and $R_3'$ are as defined in the general formula (I) above and D' corresponds to a leaving group as defined above, such as a bromine atom or a triflate group, by, for example, a method similar to that described in *J. Am. Chem. Soc.* 2001, 123 (31), 7727, or by methods described in the literature or known to the skilled person, in the presence of a copper salt in catalytic amount, in the presence of a catalytic amount of a ligand of the copper, such as a diamine, or in the presence of a base such as potassium carbonate, in a solvent such as dioxane.

In Scheme 1 the compounds of general formula (II) and the other reactants, when the method of preparing them is not described, are available commercially, are described in the literature or are prepared by analogy with processes described in the literature (D. Knittel *Synthesis* 1985, 2, 186; T. M. Williams *J. Med. Chem.* 1993, 36 (9), 1291; JP2001151771A2; WO2006024776; WO2007010138 for example).

The compounds of general formula (II) or (I) which are C-substituted on an aryl or heteroaryl group by an alkyl group may be obtained by a coupling reaction, catalyzed by a metal such as palladium or iron, which is carried out on the corresponding compounds of general formulae (II) or (I), which are substituted by a halogen atom, such as a chlorine, in the presence, for example, of an alkylmagnesium halide or an alkylzinc halide, by the methods described in the literature (A. Furstner et al. *J Am Chem Soc* 2002, 124(46), 13856; G. Queguiner et al. *J Org Chem* 1998, 63(9), 2892), for example, or methods known to the skilled person.

The compounds of general formula (II) or (I) which are C-substituted on an aryl or heteroaryl group by a cyano, aryl or heteroaryl group may be obtained by a coupling reaction, catalyzed by a metal such as palladium, which is carried out on the corresponding compounds of general formula (II) or (I) which are substituted, for example, by a bromine atom, in the presence of trimethylsilyl cyanide, arylboronic acid or heteroarylboronic acid, or by any other method described in the literature or known to the skilled person.

The compounds of general formula (II) or (I) in which P is N-substituted by a substituent $R_1$ corresponding to an aryl or heteroaryl group may be obtained by a coupling reaction, catalyzed by a metal such as copper, which is carried out on the corresponding amines of general formula (II) or (I), in the presence of an aryl or heteroaryl halide, by the Buchwald method (S. L. Buchwald et al. *J Am Chem Soc* 2002, 124, 11684), or by any other method described in the literature or known to the skilled person.

The compounds of general formula (I) or (II) which are C-substituted on an aryl or heteroaryl group by a group $NR_4R_5$, $NR_6COR_7$ or $NR_6SO_2R_8$ may be obtained from the corresponding compounds of general formula (I) or (II) which are substituted, for example, by a bromine atom, by a coupling reaction respectively with an amine, an amide or a sulfonamide in the presence of a base, a phosphine and a palladium-based catalyst, by methods which are described in the literature or known to the skilled person.

The compounds of general formula (I) or (II) which are substituted by a group $C(O)NR_4R_5$ may be obtained from the corresponding compounds of general formula (I) or (II) which are substituted by a cyano group, by methods described in the literature or known to the skilled person.

The compounds of general formula (I) or (II) which are substituted by a group —S(O)-alkyl or —S(O)$_2$-alkyl may be obtained by oxidation of the corresponding compounds of general formula (II) or (I) which are substituted by a thioalkyl group, by methods which are described in the literature or known to the skilled person.

The compounds of general formula (II) or (I) which are substituted by a group $NR_4R_5$, $NR_6COR_7$ or $NR_6SO_2R_8$ may be obtained from the corresponding compounds of general formula (II) or (I) which are substituted by a nitro group, by, for example, reduction, then acylation or sulfonylation, by methods which are described in the literature or known to the skilled person.

The compounds of general formula (II) or (I) which are substituted by a group $SO_2NR_4R_5$ may be obtained by a method similar to that described in *Pharmazie* 1990, 45, 346, or by methods which are described in the literature or known to the skilled person.

The compounds of general formula (I) or (II) in which W represents a sulfur atom may be obtained, for example, by reaction of the corresponding compounds of general formula (I) or (II) in which W represents an oxygen atom with a reactant such as Lawesson's reagent.

The compounds of general formula (I) in which $R_3$ and/or $R_3'$ represent, independently of one another, a fluorine atom may be obtained, for example, by reaction of the corresponding compounds of general formula (I) in which $R_3$ and/or $R_3'$ represent, independently of one another, a hydroxyl group, by reaction with a reactant such as diethylaminosulfur trifluoride or by any other methods known to the skilled person.

The compounds of general formula (I) in which $R_3$ and/or $R_3'$ represent, independently of one another, a $C_1$-$C_6$-alkoxy, $C_3$-$C_7$-cycloalkyloxy or $C_3$-$C_7$-cycloalkyl-$C_1$-$C_3$-alkylenoxy group may be obtained, for example, by reaction of the corresponding compounds of general formula (I) in which $R_3$ and/or $R_3'$ represent, independently of one another, a hydroxyl group by reaction with a reactant such as an alkyl halide or an alkyl sulfate in the presence of a base such as aqueous sodium hydroxide or potassium carbonate solution or by any other methods known to the skilled person.

At each step in the synthesis various groups or atoms, for example an alcohol or amine group or a nitrogen atom, may be protected by all of the methods that are known to the skilled person. The said groups or atoms may subsequently be deprotected to give the compound of general formula (I), (II) or (III) by all of the methods that are known to the skilled person.

For example, the compounds of general formula (I) for which $R_3$ corresponds to a protective group carried by a nitrogen atom, such as an ethoxycarbonyl or tert-butyloxycarbonyl group or a benzyloxycarbonyl group, may be deprotected, by chemical methods known to the skilled person, to give compounds of general formula (I) in which $R_3$ is a hydrogen atom.

The compounds of general formula (I) for which $R_3$ corresponds to a hydroxyl group may be converted, by chemical methods known to the skilled person, to give compounds of general formula (I) in which $R_3$ corresponds to an aryl-C(O)—O—, $C_1$-$C_6$-alkyl-C(O)—O—, $C_3$-$C_7$-cycloalkyl-C(O)—O—, $C_3$-$C_7$-cycloalkyl-$C_1$-$C_3$-alkylene-C(O)—O or $C_1$-$C_6$-fluoroalkyl-C(O)—O— group.

Similarly, the compounds of general formula (I) for which $R_3$ corresponds to an $NH_2$ group may be converted, by chemical methods known to the skilled person, to give compounds of general formula (I) in which $R_3$ corresponds to an $NR_6C(O)R_7$ group with $R_6$ and $R_7$ as defined in the general formula (I).

The compounds of general formula (I) for which $R_3$ corresponds to a hydroxyl group carried by an asymmetric carbon of specific configuration may be converted to compounds of general formula (I) for which $R_3$ corresponds to a hydroxyl group carried by an asymmetric carbon of inverse configuration by a two-step reaction sequence which is known to the skilled person. In a first stage, the hydroxyl group may be converted to an ester group by reaction with a carboxylic acid such as benzoic acid or acetic acid, in the presence of a reactant such as ethyl azodicarboxylate and a phosphine such as triphenylphosphine, all in solution in a solvent such as tetrahydrofuran. In a second stage, the resultant ester group may be hydrolyzed, in the presence for example of aqueous sodium hydroxide solution, to give the compounds of general formula (I) for which $R_3$ corresponds to a hydroxyl group carried by an asymmetric carbon of inverse configuration.

The compounds of general formula (III) can be used as intermediates for synthesis of compounds of formula (I).

Among the compounds of general formula (III), the invention, in another of its aspects, also provides the compounds of general formula (IV)

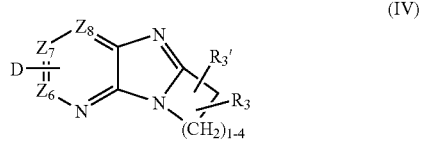

(IV)

in which $Z_6$, $Z_7$ and $Z_8$ represent, independently of one another, a carbon atom or a group C—$R_2$; one of $Z_6$, $Z_7$ and $Z_8$ corresponds to a carbon atom and carries the group D;

D represents a halogen atom or an $NH_2$ group;

$R_2$ represents a hydrogen atom;

$R_3$ and $R_3'$ represent, independently of one another, a hydrogen atom, a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, thiol, $C_1$-$C_6$-alkoxy, $C_3$-$C_7$-cycloalkyloxy, $C_3$-$C_7$-cycloalkyl-$C_1$-$C_3$-alkylenoxy, aryl-C(O)—O—, $C_1$-$C_6$-alkyl-C(O)—O—, $C_3$-$C_7$-cycloalkyl-C(O)—O—, $C_3$-$C_7$-cycloalkyl-$C_1$-$C_3$-alkylene-C(O)—O, $C_1$-$C_6$-fluoroalkyl-C(O)—O—, oxo, thiol, $NR_4R_5$, $NR_6C(O)R_7$, heteroaryl or aryl group, the heteroaryl and aryl groups being optionally substituted by one or more substituents selected from a halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano group;

or else $R_3$ and $R_3'$, together with the carbon atom which carries them, form a $C_3$-$C_7$-cycloalk-1,1-diyl group;

$R_4$ and $R_5$ represent, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_5$-alkylene or aryl group, or $R_4$ and $R_5$, together with the nitrogen atom which carries them, form an azetidine, pyrrolidine, piperidine, azepine, morpholine, thiomorpholine, piperazine or homopiperazine group, the group $NR_4R_5$ being optionally substituted by a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl, heteroaryl, aryl-S(O)$_2$—, $C_1$-$C_6$-alkyl-S(O)$_2$—, $C_1$-$C_6$-fluoroalkyl-S(O)$_2$, $C_3$-$C_7$-cycloalkyl-S(O)$_2$—, $C_3$-$C_7$-cycloalkyl-$C_1$-$C_3$-alkylene-S(O)$_2$—, aryl-C(O)—, $C_1$-$C_6$-alkyl-C(O)—, $C_3$-$C_7$-cycloalkyl-C(O)—, $C_3$-$C_7$-cycloalkyl-$C_1$-$C_3$-alkylene-C(O)—, $C_1$-$C_6$-fluoroalkyl-C(O)—, hydroxy, $C_1$-$C_6$-alkyloxy, $C_3$-$C_7$-cycloalkyloxy, $C_3$-$C_7$-cycloalkyl-$C_1$-$C_3$-alkylenoxy, $C_1$-$C_6$-fluoroalkyl, aryloxy-$C_1$-$C_6$-alkylene, aryloxy, heteroaryloxy-$C_1$-$C_6$-alkylene or heteroaryloxy group;

$R_6$ and $R_7$ represent, independently of one another, a hydrogen atom, a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group, the aryl group being optionally substituted by one or more substituents selected from a halogen atom, a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, nitro or cyano group;

or $R_6$ and $R_7$ together form a lactam of 4 to 7 members comprising the nitrogen atom and the group C(O) which carry them.

Among the compounds of general formula (IV), one group of compounds is composed of the compounds which conform to the general formula (IV'):

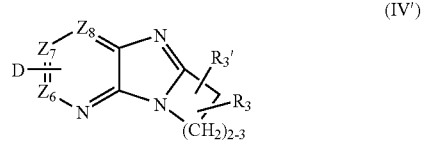

(IV')

in which $Z_6$, $Z_7$ and $Z_8$ represent, independently of one another, a carbon atom or a group C—$R_2$; one of $Z_6$, $Z_7$ and $Z_8$ corresponds to a carbon atom and carries the group D;

D represents a halogen atom or an $NH_2$ group;

$R_2$ represents a hydrogen atom;

$R_3$ and $R_3'$ represent, independently of one another, a hydrogen atom or a $C_1$-$C_6$-alkyl, hydroxyl, $C_1$-$C_6$-alkyl-C(O)—O—, $NR_4R_5$ or aryl group;

$R_4$ and $R_5$, represent, independently of one another, a hydrogen atom or a $C_1$-$C_6$-alkyl group.

The compounds of formula (IV) may contain one or more asymmetric carbon atoms. They may therefore exist in the form of enantiomers or diastereoisomers. These enantiomers and diastereoisomers and also their mixtures, including the racemic mixtures, form part of the invention.

The compounds of formula (IV) may exist in the form of bases or addition salts with acids. Such addition salts form part of the invention.

Scheme 2 illustrates the preparation of the compounds of general formula (VIII), i.e. the compounds of general formula (IV) in which the group D is bonded to the group $Z_7$, which represents a carbon atom, and $Z_6$ and $Z_8$ represent a CH group.

The compounds of general formula (VIII) may be obtained, for example, by the action of an amino ester of general formula (V), in which the alkyl chain is optionally substituted by $R_3$ and/or $R_3'$ as defined in the general formula (IV) and R represents a $C_1$-$C_6$-alkyl, phenyl or benzyl group, with a reactant of general formula (Vb) in which R' represents a halogen atom, for example a bromine atom, or a nitro group, to give a substituted product of general formula (VI).

When the group R' represents a nitro group, the reduction of the nitro groups of the compound of general formula (VI) to amino groups, in the presence for example of a catalyst such as palladium on carbon, under a hydrogen atmosphere, in suspension in a solvent such as ethanol, or by any methods of reduction that are known to the skilled person, allows access to the product of general formula (VII) in which D represents an amino group.

When the group R' represents a halogen atom, for example a bromine atom, the reduction of the nitro group of the compound of general formula (VI) to amino groups may be carried out under more chemoselective conditions such as, for example, in the presence of iron powder and an acidic aqueous solution such as an ammonium chloride solution, or by any other methods allowing access to the product of general formula (VII) in which D represents a halogen atom.

The compound of general formula (VII), finally, may be converted to a tricyclic compound of general formula (VIII) by cyclization, for example under reflux of an acidic solution such as an aqueous solution of hydrochloric acid.

Scheme 2

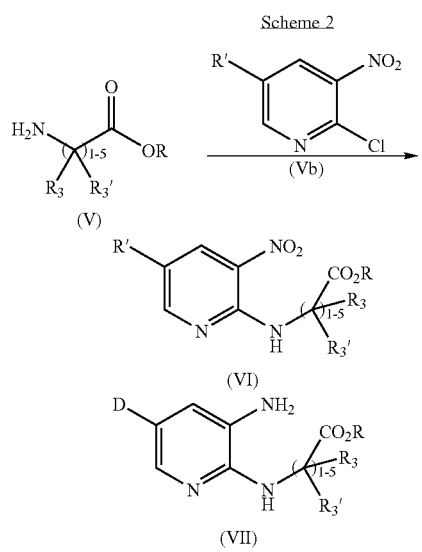

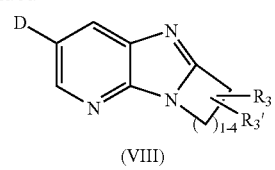

(VIII)

The compounds of general formula (IV) in which the group D is bonded either to the group $Z_6$ or to the group $Z_8$, when either the group $Z_6$ or the group $Z_8$, respectively, represents a carbon atom, may be obtained by analogy to the method described in Scheme 2.

Or alternatively, certain compounds of general formula (IV) may also be obtained, for example, by reaction of 2-(pyrrolidin-1-yl)-3,5-dinitropyridine (*Org. & Biomol. Chem.* 2003, 1(6), 1004-1011) with a Lewis acid such as zinc chloride in the presence of a reactant such as acetic anhydride (see Scheme 3). Under these conditions the tricyclic compound of general formula (IX) is isolated. The nitro group of the compound of general formula (IX) may then be reduced to give the amine of general formula (IV-b) in the presence for example of a catalyst such as palladium on carbon, under a hydrogen atmosphere, in suspension in a solvent such as ethanol, or by any methods of reduction that are known to the skilled person.

Scheme 3

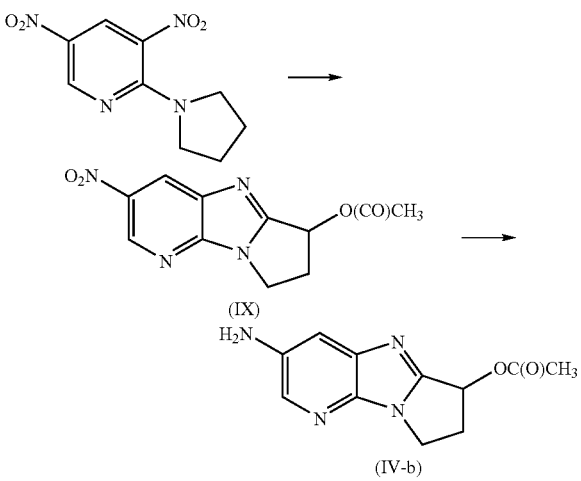

In Schemes 2 and 3, the compounds of general formula (V) and (Vb) and the other reactants, when their preparation method is not described, are available commercially, described in the literature or prepared by analogy with processes described in the literature.

Table 1 below illustrates the chemical structures and the physical properties of some examples of intermediate compounds of formula (IV) according to the invention.

In this table:

in the "salt/base" column, "–" represents a compound in free base form, whereas "HCl" represents a compound in hydrochloride form and the ratio between parentheses is the (acid:base) ratio

TABLE 1

| No. | Structure | Salt/base |
|-----|-----------|-----------|
| IV-a | H₂N-[pyrido-imidazo-pyrrolo structure] | HCl (2:1) |
| IV-b | H₂N-[pyrido-imidazo-pyrrolo with OC(O)CH₃ substituent] | — |
| IV-c | H₂N-[pyrido-imidazo-pyrrolo with OH substituent] | — |
| IV-d | H₂N-[pyrido-imidazo-tetrahydropyridine structure] | — |
| IV-e | Br-[pyrido-imidazo-pyrrolo with NH₂ substituent] | HCl |
| IV-f | H₂N-[pyrido-imidazo-pyrrolo with phenyl substituent] | — |
| IV-g | H₂N-[pyrido-imidazo-pyrrolo with two CH₃ substituents] | — |
| IV-h | H₂N-[pyrido-imidazo-pyrrolo with N(CH₃)₂ substituent] | — |

The examples which follow describe the preparation of certain intermediate compounds of formula (IV) in accordance with the invention. The numbers of the compounds exemplified refer to those of Table 1. The elemental microanalyses, the LC-MS (liquid chromatography coupled to mass spectrometry) analyses and the IR or NMR spectra confirm the structures of the compounds obtained. The compounds containing a chiral carbon were prepared from commercial chiral reactants of formula (V), and the optical rotation of the eventual compounds was measured.

EXAMPLE A

Compound IV-a 7,8-Dihydro-6H-pyrrolo[2',1':2,3]imidazo[4,5-b]pyridin-3-ylamine hydrochloride (2:1)

A.1 tert-Butyl 4-(3,5-dinitropyridin-2-yl)aminobutanoate

A suspension of 3 g (14.74 mmol) of 2-chloro-3,5-dinitropyridine in dioxane is admixed with 3.46 g (17.69 mmol) of tert-butyl 4-aminobutanoate hydrochloride and then with 4.21 ml (22.11 mmol) of triethylamine. The reaction mixture is stirred at 60° C. for 3 hours.

After return to ambient temperature, the mixture is poured onto 100 g of ice and is stirred vigorously until the ice is completely melted. The yellow precipitate formed is recovered by filtration, rinsed a number of times with water and then dried in an oven under reduced pressure. This gives 4.65 g of product in the form of a yellow powder.
$^1$H NMR (DMSO-D$_6$), δ ppm: 8.3 (s, 1H); 9.25 (s, 1H); 8.95 (s, 1H); 3.7 (q, 2H); 2.3 (t, 2H); 1.85 (quint, 2H); 1.4 (s, 9H).

A.2 tert-Butyl 4-(3,5-diaminopyridin-2-yl)aminobutanoate

A suspension of 4.2 g (12.87 mmol) of tert-butyl 4-(3,5-dinitropyridin-2-yl)aminobutanoate, obtained in the preceding step, and 1 g of 10% palladium on carbon in 50 ml of ethanol is stirred vigorously at ambient temperature for 3 hours under 5 atm of hydrogen.

After this time the mixture is filtered on celite, rinsing with ethanol. The filtrate is subsequently concentrated under reduced pressure to give tert-butyl 4-(3,5-diamino-pyridin-2-yl)aminobutanoate, which will be used as it is in the following step.
$^1$H NMR (DMSO D$_6$), δ (ppm): 6.9 (s, 1H); 6.2 (s, 1H); 4.7 (m, 1H); 4.5 (m, 2H); 3.35 (m, 2H); 3.2 (m, 2H); 2.3 (m, 2H); 1.75 (m, 2H); 1.4 (s, 9H).

A.3 7,8-Dihydro-6H-pyrrolo[2',1':2,3]imidazo[4,5-b]pyridin-3-ylamine hydrochloride (2:1)

A solution of 3 g (11.26 mmol) of tert-butyl 4-(3,5-diaminopyridin-2-yl)aminobutanoate, obtained in the preceding step, in 100 ml of 6N hydrochloric acid is heated at reflux for 12 hours.

After this time the mixture is cooled to ambient temperature and then concentrated under reduced pressure. The rubbery residue which results is taken up in 50 ml of ethanol and then concentrated under reduced pressure. This operation is repeated three times until a powder is obtained which is taken up in 100 ml of boiling diisopropyl ether. The suspension is filtered while hot and dried to give 2.56 g of product in hydrochloride form.
$^1$H NMR (DMSO-D$_6$), δ ppm: 8.25 (s, 1H); 7.7 (s, 1H); 6.2 (broad s, NH$_2$); 4.3 (t, 2H); 3.3 (t, 2H); 2.8 (quint, 2H).

EXAMPLE B

Compound IV-b

3-Amino-7,8-dihydro-6H-pyrrolo[2',1':2,3]imidazo[4,5-b]pyridin-6-yl acetate

B.1 3-Nitro-7,8-dihydro-6H-pyrrolo[2',1':2,3]imidazo[4,5-b]pyridin-6-yl acetate A mixture of 1 g (4.2 mmol) of 2-(pyrrolidin-1-yl)-3,5-dinitropyridine (*Org. & Biomol. Chem.* 2003, 1(6), 1004-1011) and 0.584 g (4.2 mmol) of zinc chloride in 10 ml of acetic anhydride is heated at reflux for six hours. After this time a further 0.584 g (4.2 mmol) of zinc chloride are added and the stirring at reflux is maintained for eighteen hours. After this time the mixture is poured onto 100 g of ice and then extracted with three times 50 ml of ethyl acetate. The organic phases are combined and then washed with twice 20 ml of saturated sodium hydrogen carbonate solution, once with 20 ml of water and then once with 50 ml of saturated sodium chloride solution, then dried over sodium sulfate and concentrated under reduced pressure. The product obtained is purified by chromatography on a silica column, eluting with a mixture of ethyl acetate and n-heptane. The resulting product is recrystallized from a mixture of diisopropyl ether and isopropanol. This gives 0.29 g of the expected compound.

$^1$H NMR (DMSO D$_6$), δ (ppm): 9.28 (s, 1H); 8.91 (s, 1H); 6.27 (m, 1H); 4.42 (m, 1H); 4.3 (m, 1H); 3.18 (m, 1H); 2.65 (m, 1H); 2.11 (s, 3H).

B.2 3-Amino-7,8-dihydro-6H-pyrrolo[2',1':2,3]imidazo[4,5-b]pyridin-6-yl acetate A suspension of 0.25 g (0.95 mmol) of 3-nitro-7,8-dihydro-6H-pyrrolo[2',1':2,3]imidazo[4,5-b]pyridin-6-yl acetate, obtained in the preceding step, and 0.21 g of 10% palladium on carbon in 60 ml of ethanol is stirred at 20° C. for 3 hours under five atmospheres of hydrogen. After this time the mixture is filtered on a bed of celite and then concentrated under reduced pressure. This gives 0.22 g of the expected product, which will be used as it is in the remainder of the synthesis.

$^1$H NMR (DMSO D$_6$), δ (ppm): 7.85 (s, 1H); 7.2 (s, 1H); 6.1 (m, 1H); 5.05 (s, 2H); 4.2 (m, 1H); 4.1 (m, 1H); 3.1 (m, 1H); 2.55 (m, 1H); 2.11 (s, 3H).

EXAMPLE C

Compound IV-c

(−)-3-Amino-7,8-dihydro-6H-pyrrolo[2',1':2,3]imidazo[4,5-b]pyridin-6-ol

C.1 Methyl 4-[(3,5-dinitropyridin-2-yl)amino]-2-hydroxybutyrate

A mixture of 2.8 g (13.48 mmol) of 2-chloro-3,5-dinitropyridine, 2.75 g (16.2 mmol) of methyl(S)-4-amino-2-hydroxybutyrate hydrochloride and 3.41 g (2.5 mmol) of triethylamine in 50 ml of dioxane is heated at 65° C. for four hours.

After this time, the reaction mixture is concentrated under reduced pressure and the residue is taken up in 50 ml of water. The mixture is extracted with two times 50 ml of dichloromethane. The organic phases are combined, washed with 50 ml of saturated sodium carbonate solution, dried over sodium sulfate and then concentrated under reduced pressure.

The oil obtained is purified by chromatography on a silica column, eluting with a mixture of dichloromethane and methanol. This gives 2.1 g of the expected product, which is used as it is in the remainder of the synthesis.

MS: [MH]$^+$=301

$^1$H NMR (CDCl$_3$), δ (ppm): 9.33 (d, 1H); 9.3 (d, 1H); 9.21 (broadened singlet, 1H); 4.42 (m, 1H); 4.01 (m, 2H); 3.88 (s, 3H); 3.21 (d, 1H); 2.37 (m, 1H); 2.12 (m, 1H).

C.2 Methyl 4-[(3,5-diaminopyridin-2-yl)amino]-2-hydroxybutyrate

A suspension of 1.9 g (6.33 mmol) of methyl 4-[(3,5-dinitropyridin-2-yl)amino]-2-hydroxybutyrate, obtained in the preceding step, and 0.1 g of 10% palladium on carbon in 100 ml of methanol is stirred vigorously at 20° C. for seven hours under five atmospheres of hydrogen. After this time the mixture is filtered on a bed of celite and then concentrated under reduced pressure. This gives 1.45 g of the expected product, which is used as it is in the remainder of the synthesis.

C.3 (−)-3-Amino-7,8-dihydro-6H-pyrrolo[2',1':2,3]imidazo[4,5-b]pyridin-6-ol A solution of 1.4 g (5.83 mmol) of methyl 4-[(3,5-diaminopyridin-2-yl)amino]-2-hydroxybutyrate, obtained in the preceding step, in 50 ml of 6N hydrochloric acid is stirred at reflux for fifteen hours. After this time the mixture is concentrated under reduced pressure to a volume of 10 ml. The pH of the solution is adjusted to 10 by successive additions of sodium carbonate and then the mixture is concentrated under reduced pressure and the resulting solid is triturated with 100 ml of a 10% solution of methanol in dichloromethane. The mixture is filtered and the operation is repeated three times. The filtrates are combined and concentrated under reduced pressure and the resulting product is purified by chromatography on a silica column, eluting with a mixture of dichloromethane and methanol. This gives 0.3 g of the expected product.

mp=229-230° C.

[α]$_D^{20}$=−17.43, c=0.175 g/100 ml; DMSO

MS: [MH]$^+$=191

$^1$H NMR (DMSO D$_6$), δ (ppm): 7.77 (s, 1H); 7.19 (s, 1H); 5.80 (d, 1H); 5.08 (m, 1H); 4.93 (broadened peak, 2H); 4.17 (m, 1H); 3.99 (m, 1H); 2.91 (m, 1H); 2.39 (m, 1H).

EXAMPLE D

Compound IV-d

6,7,8,9-Tetrahydroimidazo[1,2-a:5,4-b']dipyridin-3-amine

D.1 Ethyl 5-[(3,5-dinitropyridin-2-yl)amino]pentanoate

A procedure similar to that of the method described in step C.1 is carried out, starting from 1.2 g (5.9 mmol) of 2-chloro-3,5-dinitropyridine, 1.03 g (7.07 mmol) of ethyl 5-aminovalerate and 0.9 g (8.84 mmol) of triethylamine in 20 ml of dioxane. This gives 1.4 g of expected product.

m.p.=70-72° C.

MS: [MH]$^+$=313

$^1$H NMR (CDCl$_3$), δ (ppm): 9.18 (m, 2H); 8.73 (broadened peak, 1H); 4.08 (q, 2H); 3.70 (m, 2H); 2.32 (m, 2H); 1.70 (m, 4H); 1.19 (t, 3H).

D.2 Ethyl 5-[(3,5-diaminopyridin-2-yl)amino]pentanoate

A procedure similar to the method described in step C.2 is carried out, starting from 1.35 g (4.32 mmol) of the compound prepared in the preceding step and 100 mg of 10% palladium on carbon in suspension in 100 ml of methanol. This gives 1.1 g of the expected product, which is used as it is in the remainder of the synthesis.

D.3 6,7,8,9-Tetrahydroimidazo[1,2-a:5,4-b']dipyridin-3-amine

A procedure similar to the method described in step C.3 is carried out, starting from 1.1 g (4.36 mmol) of the product obtained in the preceding step, in solution in 30 ml of 6N hydrochloric acid. The product obtained is purified by chromatography on a neutral alumina column, eluting with a mixture of dichloromethane and methanol. This gives 60 mg of the expected product, which is used as it is in the remainder of the synthesis.

MS: $[MH]^+=189$ $^1$H NMR (CDCl$_3$), δ (ppm): 7.79 (s, 1H); 7.20 (s, 1H); 4.09 (t, 2H); 3.49 (broadened peak, 2H); 2.88 (t, 2H); 1.99 (m, 4H)

EXAMPLE E

Compound IV-e

3-Bromo-7,8-dihydro-6H-pyrrolo[2',1':2,3]imidazo[4,5-b]pyridin-6-amine hydrochloride

E.1 tert-Butyl 4-[(5-bromo-3-nitropyridin-2-yl)amino]-2-tert-butoxycarbonylamino-butanoate A procedure similar to the method described in step C.1 is carried out, starting from 2 g (8.42 mmol) of 5-bromo-2-chloro-3-nitropyridine, 3.14 g (10.11 mmol) of tert-butyl(S)-4-amino-2-tert-butoxycarbonylaminobutanoate hydrochloride and 2.31 g (16.85 mmol) of triethylamine in 30 ml of dioxane. This time the mixture is heated for 12 hours. This gives 3.71 g of the expected product, which is used as it is in the remainder of the synthesis.

MS: $[MH]^+=475$ $^1$H NMR (DMSO D$_6$), δ (ppm): 8.59 (s, 2H); 8.52 (m, 1H); 7.18 (d, 1H); 3.91 (m, 1H); 3.68 (m, 2H); 1.94 (m, 2H) 1.4 (s, 18H).

E.2 tert-Butyl 4-[(3-amino-5-bromopyridin-2-yl)amino]-2-tert-butoxycarbonylamino-butanoate A suspension of 3.5 g of tert-butyl 4-[(5-bromo-3-nitropyridin-2-yl)amino]-2-tert-butoxycarbonylaminobutanoate, 1.23 g (22 mmol) of iron powder and 20 g (0.373 mol) of ammonium chloride in 40 ml of a 1:1 mixture of ethanol and tetrahydrofuran is heated at reflux for two hours. After this time the reaction mixture is filtered on a bed of celite, which is rinsed with 100 ml of ethanol. The filtrate is concentrated under reduced pressure and then the residue is taken up in 20 ml of water. The mixture is then extracted with three times 50 ml of ethyl acetate. The organic phases are combined, washed with 50 ml of a saturated aqueous sodium chloride solution, dried over sodium sulfate and then concentrated under reduced pressure. An oil is recovered which is purified by chromatography on a silica column, eluting with a mixture of dichloromethane and methanol. This gives 2.93 g of the expected product in the form of a solid, used as it is in the remainder of the synthesis.

MS: $[MH]^+=445$ $^1$H NMR (DMSO D$_6$), δ (ppm): 7.39 (s, 1H); 7.21 (d, 1H); 6.81 (s, 1H); 5.70 (broadened peak, 1H); 5.07 (broadened peak, 2H); 3.91 (m, 1H); 3.32 (m, 2H); 1.98 (m, 1H); 1.81 (m, 1H); 1.4 (s, 18H).

E.3 (+)-3-Bromo-7,8-dihydro-6H-pyrrolo[2',1:2,3]imidazo[4,5-b]pyridin-6-amine hydrochloride (IV-e)

A procedure similar to the method described in step C.3 is carried out, starting from 2.75 g (5.56 mmol) of tert-butyl 4-(3-amino-5-bromopyridin-2-ylamino)-2-tert-butoxycarbonylaminobutanoate and 40 ml of 6N hydrochloric acid. After cooling to 20° C., the reaction mixture is successively concentrated under reduced pressure, taken up in 50 ml of ethanol and concentrated under reduced pressure, to give a solid which is triturated with hot isopropyl ether. Filtration gives 1.31 g of a powder, which is used as it is in the remainder of the synthesis.

MS: $[MH]^+=253$ $[\alpha]_D^{20}=+23.81°$, c=0.113 g/100 ml; MeOH $^1$H NMR (DMSO D$_6$), δ (ppm): 9.11 (broadened peak, 2H); 8.49 (s, 1H); 8.43 (s, 1H); 4.96 (m, 1H); 4.4 (m, 1H); 4.23 (m, 1H); 3.12 (m, 1H); 2.73 (m, 1H).

(+)-3-Bromo-7,8-dihydro-6H-pyrrolo[2',1':2,3]imidazo[4,5-b]pyridin-6-amine (IV-e)

The amine (IV-e) in base form was obtained in a conventional manner from a hydrochloride solution in water, by adjusting the pH by successively adding aqueous ammonia solution, then by extraction with ethyl acetate solution and concentration under reduced pressure.

$^1$H NMR (DMSO D$_6$), δ (ppm): 8.4 (d, 1H); 8.25 (d, 1H); 4.4 (m, 1H); 4.25 (m, 1H); 4.1 (m, 1H); 2.9 (m, 1H); 2.3 (m, 1H); 2.2 (broadened peak, 2H). $[\alpha]_D^{20}=+0.568°$, c=1.004 g/100 ml; MeOH

EXAMPLE F

Compound IV-f

6-Phenyl-7,8-dihydro-6H-pyrrolo[2',1':2,3]imidazo[4,5-b]pyridin-3-amine

F.1 Methyl 4-amino-2-phenylbutyrate hydrochloride

A mixture of 1 g (4.64 mmol) of 4-amino-2-phenylbutyric acid hydrochloride and 0.67 ml (5.1 mmol) of trimethylsilyl chloride in 50 ml of methanol is heated at reflux for 2 hours. The mixture is subsequently stirred at 20° C. for 12 hours and then concentrated under reduced pressure, triturated in 50 ml of ethyl ether and then filtered. This gives 0.9 g of the expected product in the form of a white solid.

MS: $[MH]^+=194$

F.2 Methyl 4-(3,5-dinitropyridin-2-ylamino)-2-phenylbutyrate

A procedure similar to the method described in step C.1 is carried out, starting from 0.8 g (3.93 mmol) of 2-chloro-3,5-dinitropyridine and 1 g (4.32 mmol) of methyl 4-amino-2-phenylbutyrate. This gives 1.1 g of expected product.

¹H NMR (CDCl₃), δ (ppm): 9.29 (m, 2H); 8.79 (broadened peak, 1H); 7.38 (m, 5H); 3.8 (m, 3H); 3.74 (s, 3H); 2.6 (sext., 1H); 2.31 (sext., 1H).

F.3 Methyl 4-(3,5-diaminopyridin-2-ylamino)-2-phenylbutyrate

A procedure similar to the method described in step C.2 is carried out, starting from 1.1 g (3.05 mmol) of methyl 4-(3,5-dinitropyridin-2-ylamino)-2-phenylbutyrate. This gives 0.9 g of the expected product, which is used as it is in the remainder of the synthesis.
MS: [MH]⁺=301

F.4 6-Phenyl-7,8-dihydro-6H-pyrrolo[2',1':2,3]imidazo[4,5-b]pyridin-3-amine (IV-f)

A procedure similar to the method described in step C.3 is carried out, starting from 0.9 g (3.3 mmol) of methyl 4-(3,5-diaminopyridin-2-ylamino)-2-phenylbutyrate. This gives 0.88 g of the expected product, which is used as it is in the remainder of the synthesis.
MS: [MH]⁺=251
¹H NMR (CDCl₃), δ (ppm): 7.78 (d, 1H); 7.2 (m, 6H); 4.43 (m, 1H); 4.29 (m, 1H); 4.11 (m, 1H); 3.5 (broadened peak, 2H); 3.09 (m, 1H); 2.62 (m, 1H).

EXAMPLE G

Compound IV-g

6,6-Dimethyl-7,8-dihydro-6H-pyrrolo[2',1':2,3]imidazo[4,5-b]pyridin-3-amine (IV-g)

G.1 Methyl 4-amino-2,2'-dimethylbutyrate hydrochloride

A procedure similar to the method described in step F.1 is carried out, starting from 1 g (5.97 mmol) of 4-amino-2,2'-dimethylbutyric acid. This gives 1.04 g of expected product.
¹H NMR (DMSO D₆), δ (ppm): 8.03 (broadened peak, 2H); 3.67 (s, 3H); 2.71 (m, 2H); 1.8 (m, 2H); 1.15 (s, 6H).

G.2 Methyl 4-[(3,5-dinitropyridin-2-yl)amino]-2,2'-dimethylbutyrate

A procedure similar to the method described in step C.1 is carried out, starting from 0.9 g (4.42 mmol) of 2-chloro-3,5-dinitropyridine and 0.96 g (5.31 mmol) of methyl 4-amino-2,2'-dimethylbutyrate hydrochloride, prepared in the preceding step. After 5 hours of stirring at 70° C., the reaction mixture, after cooling, is poured into 100 ml of ice-water. The resulting solution is extracted with three times 50 ml of dichloromethane. The organic phases are combined, washed with 50 ml of water, dried over sodium sulfate and then concentrated under reduced pressure. This gives 1.5 g of the expected compound, which is used as it is in the remainder of the synthesis.
¹H NMR (CDCl₃), δ (ppm): 9.33 (d, 1H); 9.29 (d, 1H); 8.82 (broadened peak, 1H); 3.87 (m, 2H); 3.78 (s, 3H); 2.08 (m, 2H); 1.35 (s, 6H).

G.3 Methyl 4-[(3,5-diaminopyridin-2-yl)amino]-2,2'-dimethylbutyrate

A procedure similar to the method described in step C.2 is carried out, starting from 1.05 g (3.36 mmol) of methyl 4-[(3,5-dinitropyridin-2-yl)amino]-2,2'-dimethylbutyrate, obtained in the preceding step. This gives 1 g of the expected product.
¹H NMR (DMSO D₆), δ (ppm): 6.79 (d, 1H); 6.31 (d, 1H); 5.5-4.2 (broadened peak, 5H); 3.61 (s, 3H); 3.15 (m, 2H); 1.82 (m, 2H); 1.19 (s, 6H).

G.4 6,6-Dimethyl-7,8-dihydro-6H-pyrrolo[2',1':2,3]imidazo[4,5-b]pyridin-3-amine (IV-g)

A procedure similar to the method described in step C.3 is carried out, starting from 1 g (3.96 mmol) of methyl 4-[(3,5-diaminopyridin-2-yl)amino]-2,2'-dimethylbutyrate, obtained in the preceding step. This gives 0.400 g of expected product.
¹H NMR (CDCl₃), δ (ppm): 8.04 (d, 1H); 7.47 (d, 1H); 4.11 (m, 1H); 2.48 (m, 2H); 1.41 (s, 6H).
MS: [MH]⁺=203

EXAMPLE H

Compound IV-h

N,N-Dimethyl-3-bromo-7,8-dihydro-6H-pyrrolo[2',1':2,3]imidazo[4,5-b]pyridin-6-amine (IV-h)

A solution of 0.5 g (1.5 mmol) of compound IV-e in hydrochloride form in 10 ml of methanol is eluted on an ion exchange cartridge. Following concentration under reduced pressure of the eluted solution, this gives 0.37 g of 3-bromo-7,8-dihydro-6H-pyrrolo[2',1':2,3]imidazo[4,5-b]pyridin-6-amine, which is taken up in 10 ml of acetonitrile. Subsequently 0.52 ml (6.91 mmol) of a 37% aqueous formaldehyde solution is added. The reaction mixture is stirred for 20 minutes and then 0.183 g (2.77 mmol) of sodium cyanoborohydride is added. After 20 minutes of further stirring, 0.5 ml of glacial acetic acid is added and the mixture is stirred at 20° C. for three hours. The solution is subsequently diluted with 30 ml of a mixture of dichloromethane and methanol. The organic phase is separated off, washed with three times 20 ml of 1M sodium hydroxide solution, dried over sodium sulfate and then concentrated under reduced pressure. This gives 0.292 g of the expected product, which is used as it is in the remainder of the synthesis.
MS: [MH]⁺=281
$[\alpha]_D^{20}$=not determined The examples which follow describe the preparation of certain compounds in accordance with the invention. These examples are not limitative, and merely illustrate the present invention. The numbers of the compounds exemplified refer to those in Table 2. The elemental microanalyses, LC-MS (liquid chromatography coupled to mass spectrometry) analyses and/or IR or NMR spectra confirm the structures of the compounds obtained. The optical rotation or the enantiomeric purity associated with a retention time of the eventual compounds containing a chiral carbon were measured.

EXAMPLE 1

Compound 1

N-(7,8-Dihydro-6H-pyrrolo[2',1':2,3]imidazo[4,5-b]pyridin-3-yl)-5-fluoro-1-(3-fluorobenzyl)-1H-indole-2-carboxamide

1.1 5-Fluoro-1-(3-fluorobenzyl)-1H-indole-2-carboxylic acid

An aqueous sodium hydroxide solution prepared from 1.15 g (28.92 mmol) of sodium hydroxide pellets in 50 ml of water is added to a solution of 7.6 g (24.10 mmol) of ethyl 5-fluoro-1-(3-fluorobenzyl)-1H-indole-2-carboxylate (WO2006/024776) in 241 ml of ethanol. The mixture is heated for two hours and then concentrated under reduced pressure. The resulting solid is taken up in 200 ml of water. The solution is washed with two times 100 ml of ethyl ether, acidified by successive additions of small amounts of concentrated hydrochloric acid and then extracted with 200 ml of ethyl acetate. The organic phase is finally washed with twice 100 ml of water, once with 50 ml of saturated sodium chloride solution, and dried over magnesium sulfate and concentrated under reduced pressure. This gives, after drying at 50° C. under reduced pressure, 6.4 g of the expected product, in the form of a solid which will be used as it is in the remainder of the synthesis.

1.2 N-(7,8-Dihydro-6H-pyrrolo[2',1':2,3]imidazo[4,5-b]pyridin-3-yl)-5-fluoro-1-(3-fluorobenzyl)-1H-indole-2-carboxamide (Compound 1)

A solution of 0.5 g (1.74 mmol) of 5-fluoro-1-(3-fluorobenzyl)-1H-indole-2-carboxylic acid, prepared in sep 1.1, 0.33 g (1.74 mmol) of N-(3-dimethylaminopropyl)-N'-ethylcarbodiimide and 0.23 g (1.74 mmol) of N-1-hydroxybenzotriazole in 10 ml of dimethylformamide is stirred at 20° C. for 15 minutes. The reaction mixture is subsequently admixed with 0.516 g (2.09 mmol) of the compound IV-a and also with 0.29 ml (2.09 mmol) of triethylamine. The reaction mixture is subsequently stirred at 20° C. for 12 hours and then concentrated under reduced pressure, poured into 50 ml of water and extracted with three times 50 ml of ethyl acetate. The organic phases are combined and then washed with twice 20 ml of saturated sodium hydrogen carbonate solution, once with 20 ml of water and then once with 50 ml of saturated sodium chloride solution, dried over sodium sulfate and then concentrated under reduced pressure. The product obtained is purified by chromatography on a silica column, eluting with a mixture of dichloromethane and methanol. This gives 0.31 g of the expected compound.

Melting point: 227-229° C.
MS: $[MH]^+=444$
$^1$H NMR (DMSO D$_6$), δ (ppm): 10.6 (s, 1H); 8.63 (s, 1H); 8.3 (s, 1H); 7.59 (m, 2H); 7.48 (s, 1H); 7.33 (m, 1H); 7.18 (m, 1H); 7.05 (m, 1H); 6.92 (m, 2H); 5.91 (s, 2H); 4.15 (t, 2H); 3 (t, 2H); 2.68 (m, 2H).

EXAMPLE 2

Compound 2

N-(6-Acetoxy-7,8-dihydro-6H-pyrrolo[2',1':2,3]imidazo[4,5-b]pyridin-3-yl)-5-fluoro-1-(3-fluorobenzyl)-1H-indole-2-carboxamide A solution of 0.25 g (0.87 mmol) of 5-fluoro-1-(3-fluorobenzyl)-1H-indole-2-carboxylic acid, prepared in step 1.1, 0.166 g (0.87 mmol) of N-(3-dimethylaminopropyl)-N'-ethylcarbodiimide and 0.117 g (0.87 mmol) of N-1-hydroxybenzotriazole in 3 ml of dimethylformamide is stirred at 20° C. for 15 minutes. The reaction mixture is subsequently admixed with 0.245 g (1.04 mmol) of 6-acetoxy-7,8-dihydro-6H-pyrrolo[2',1':2,3]imidazo[4,5-b]pyridin-3-amine (compound IV-b), in solution in 3 ml of dimethylformamide. The reaction mixture is subsequently stirred at 20° C. for 16 hours and then concentrated under reduced pressure, poured into 50 ml of water and extracted with three times 50 ml of ethyl acetate. The organic phases are combined, then washed with twice 20 ml of saturated sodium hydrogen carbonate solution, once with 20 ml of water and then once with 50 ml of saturated sodium chloride solution, dried over sodium sulfate and then concentrated under reduced pressure. The product obtained is purified by chromatography on a silica column, eluting with a mixture of dichloromethane and methanol. The product thus purified is finally triturated in hot diisopropyl ether and filtered while hot to give 0.27 g of the expected product.

Melting point: 139-141° C.
MS: $[MH]^+=502$
$^1$H NMR (DMSO D$_6$), δ (ppm): 10.69 (s, 1H); 8.69 (s, 1H); 8.44 (s, 1H); 7.61 (m, 2H); 7.5 (s, 1H); 7.35 (m, 1H); 7.19 (m, 1H); 7.05 (m, 1H); 6.92 (m, 2H); 6.18 (m, 1H); 5.91 (s, 2H); 4.33 (m, 1H); 4.22 (t, 1H); 3.17 (m, 1H); 2.6 (m, 1H); 2.1 (s, 3H).

EXAMPLE 3

Compound 3

N-(6-Hydroxy-7,8-dihydro-6H-pyrrolo[2',1':2,3]imidazo[4,5-b]pyridin-3-yl)-5-fluoro-1-(3-fluorobenzyl)-1H-indole-2-carboxamide A suspension of 0.2 g (0.4 mmol) of compound 2 prepared in Example 2 and 0.225 g (1.6 mmol) of cesium carbonate in 5 ml of methanol is stirred at 20° C. for two hours. After this time the reaction mixture is concentrated under reduced pressure, poured into 50 ml of water and extracted with three times 20 ml of dichloromethane. The organic phases are combined and then washed once with 20 ml of water and then once with 50 ml of saturated sodium chloride solution, dried over sodium sulfate and then concentrated under reduced pressure. The product obtained is purified by chromatography on a silica column, eluting with a mixture of dichloromethane and methanol, and then recrystallized from a mixture of ethanol and water. This gives 110 mg of the expected product.

Melting point: 288-290° C.
MS: $[MH]^+=460$
$^1$H NMR (DMSO D6), δ (ppm): 8.62 (s, 1H); 8.42 (s, 1H); 7.61 (m, 2H); 7.48 (s, 1H); 7.34 (m, 1H); 7.19 (m, 1H); 7.06 (m, 1H); 6.92 (m, 2H); 5.99 (d, 1H); 5.91 (s, 2H); 5.17 (m, 1H); 4.29 (m, 1H); 4.1 (m, 1H); 2.95 (m, 1H); 2.45 (m, 1H).

EXAMPLE 4

Compound 26

N-(6-Hydroxy-7,8-dihydro-6H-pyrrolo[2',1':2,3]imidazo[4,5-b]pyridin-3-yl)-5-trifluoromethyl-1-(3-fluorobenzyl)-1H-indole-2-carboxamide A procedure similar to the method described in step 1.2 is carried out, starting from 0.4 g (1.18 mmol) of 5-trifluoromethyl-1-(3-fluorobenzyl)-1H-indole-2-carboxylic acid (WO2006072736), 0.29 g (1.54 mmol) of compound (IV-c), 0.25 g (1.3 mmol) of N-(3-dimethylaminopropyl)-N'-ethylcarbodiimide hydrochloride and 0.18 g (1.3 mmol) of N-1-hydroxybenzotriazole in 12 ml of dimethylformamide. This gives 460 mg of the expected product.

m.p.=267-268° C.
MS: $[MH]^+=510$
enantiomeric purity=94%; retention time=14.5 nm
$[\alpha]_D^{20}=-1.327°$, c=0.211 g/100 ml (DMSO)
$^1$H NMR (DMSO D$_6$), δ (ppm): 10.79 (s, 1H); 8.61 (s, 1H); 8.41 (s, 1H); 8.24 (s, 1H); 7.81 (d, 1H); 7.65 (s, 1H); 7.61 (m, 1H); 7.36 (m, 1H); 7.09 (m, 1H); 6.96 (d, 2H); 6 (s, 2H); 5.18 (m, 1H); 4.29 (m, 1H); 4.12 (m, 1H); 2.97 (m, 1H); 2.43 (m, 1H).

EXAMPLE 5

Compound 27

N-(6,7,8,9-Tetrahydroimidazo[1,2-a:5,4-b']dipyridin-3-yl)-5-trifluoromethyl-1-(3-fluorobenzyl)-1H-indole-2-carboxamide A procedure similar to the method described in step 1.2 is carried out, starting from 0.06 g (0.18 mmol) of 5-trifluoromethyl-1-(3-fluorobenzyl)-1H-indole-2-carboxylic acid (WO2006072736), 0.05 g (0.27 mmol) of compound (IV-d), 0.038 g (0.2 mmol) of N-(3-dimethylaminopropyl)-N'-ethyl-carbodiimide hydrochloride and 0.027 g (0.2 mmol) of N-1-hydroxybenzotriazole in 2 ml of dimethylformamide. This gives 70 mg of the expected product.

m.p.=262-263° C.
MS: $[MH]^+$=508
$^1$H NMR (DMSO D$_6$), δ (ppm): 10.75 (s, 1H); 8.56 (d, 1H); 8.30 (d, 1H); 8.22 (s, 1H); 7.81 (d, 1H); 7.62 (s, 1H); 7.59 (dxd, 1H); 7.34 (q, 1H); 7.07 (txd, 1H); 6.94 (d, 2H); 5.99 (s, 2H); 4.15 (m, 2H); 3.01 (m, 2H); 2.09 (m, 2H); 1.95 (m, 2H).

EXAMPLE 6

Compound 30

N-(6-Phenyl-7,8-dihydro-6H-pyrrolo[2',1':2,3]imidazo[4,5-b]pyridin-3-yl)-5-trifluoromethyl-1-(3-fluorobenzyl)-1H-indole-2-carboxamide A mixture of 50 mg (0.15 mmol) of 5-trifluoromethyl-1-(3-fluorobenzyl)-1H-indole-2-carboxylic acid (WO2006072736), 44.5 mg (0.18 mmol) of compound (IV-f) and 29 mg (0.18 mmol) of diethyl cyanophosphonate in solution in 6 ml of dimethylformamide is stirred at 20° C. for 30 minutes. Subsequently 22.5 mg (0.22 mmol) of triethylamine are added and then the mixture is stirred at 20° C. for 12 hours. After this time the mixture is concentrated under reduced pressure, taken up in 50 ml of water and then extracted with three times 50 ml of ethyl acetate. The organic phases are combined, washed with 20 ml of water and then dried over sodium sulfate and concentrated under reduced pressure. The resulting product is subsequently purified by chromatography on a silica column, eluting with a mixture of dichloromethane and methanol. This gives 75 mg of the expected product.

m.p.=129-130° C.
MS: $[MH]^+$=570
$^1$H NMR (DMSO D$_6$), δ (ppm): 10.75 (s, 1H); 8.62 (s, 1H); 8.31 (s, 1H); 8.21 (s, 1H); 7.81 (d, 1H); 7.65 (s, 1H); 7.61 (d, 1H); 7.4 (m, 5H); 7.32 (m, 1H); 7.08 (m, 1H); 6.93 (d, 2H); 5.98 (s, 2H); 4.68 (m, 1H); 4.41 (m, 1H); 4.22 (m, 1H); 3.2 (m, 1H); 2.68 (m, 1H).

EXAMPLE 7

Compound 31

N-(6,6-Dimethyl-7,8-dihydro-6H-pyrrolo[2',1':2,3]imidazo[4,5-b]pyridin-3-yl)-5-trifluoromethyl-1-(3-fluorobenzyl)-1H-indole-2-carboxamide A procedure similar to that of Example 6 is carried out, starting from 0.2 g (0.59 mmol) of 5-trifluoromethyl-1-(3-fluorobenzyl)-1H-indole-2-carboxylic acid (WO2006072736) and 0.17 g (0.71 mmol) of compound (IV-h). This gives 25 mg of the expected product.

m.p.=212-213° C.
MS: $[MH]^+$=522
$^1$H NMR (DMSO D$_6$), δ (ppm): 10.7 (s, 1H); 8.58 (d, 1H); 8.29 (d, 1H); 8.22 (s, 1H); 7.83 (d, 1H); 7.63 (s, 1H); 7.59 (m, 1H); 7.35 (m, 1H); 7.07 (m, 1H); 6.96 (m, 2H); 5.96 (s, 2H); 4.2 (m, 2H); 3.2 (m, 1H); 2.49 (m, 1H); 1.39 (s, 6H).

EXAMPLE 8

Compound 32

N-(6-Hydroxy-7,8-dihydro-6H-pyrrolo[2',1':2,3]imidazo[4,5-b]pyridin-3-yl)-5-trifluoromethyl-1-(3-fluorobenzyl)-1H-indole-2-carboxamide 8.1 3-[[[1-(3-Fluorobenzyl)-5-trifluoromethyl-1H-indol-2-yl]carbonyl]amino]-7,8-dihydro-6H-pyrrolo[2',1':2,3]imidazo[4,5-b]pyridin-6-yl pyridine-2-carboxylate A mixture, stirred at −20° C. under an inert atmosphere, of 0.12 g (0.24 mmol) of (−)-N-(6-hydroxy-7,8-dihydro-6H-pyrrolo[2',1':2,3]imidazo[4,5-b]pyridin-3-yl)-5-trifluoromethyl-1-(3-fluorobenzyl)-1H-indole-2-carboxamide (compound 26), 0.116 g (0.94 mmol) of picolinic acid and 0.247 g (0.94 mol) of triphenylphosphine in 5 ml of tetrahydrofuran is admixed dropwise with 0.19 g (0.94 mmol) of diisopropyl azodicarboxylate. After 16 hours of stirring at 20° C., the reaction mixture is concentrated under reduced pressure and then taken up in 20 ml of dichloromethane and 20 ml of saturated sodium hydrogen carbonate solution. The organic phase is separated, washed with water, dried over sodium sulfate and then concentrated under reduced pressure. The product obtained is purified by chromatography on a silica column, eluting with a mixture of dichloromethane, acetone and methanol.

This gives 0.1 g of expected product.
MS: $[MH]^+$=615
$^1$H NMR (DMSO D$_6$), δ (ppm): 10.8 (s, 1H); 8.75 (m, 1H); 8.7 (m, 1H); 8.48 (m, 1H); 8.25 (s, 1H); 8.15 (dd, 1H); 8.05 (m, 1H); 7.82 (dd, 1H); 7.7 (ddd, 1H); 7.65 (s, 1H); 7.6 (dd, 1H); 7.35 (ddd, 1H); 7.08 (ddd, 1H); 6.95 (m, 2H); 6.5 (dd, 1H); 6.0 (s, 2H); 4.4 (m, 1H); 4.3 (m, 1H); 3.3 (m, 1H); 2.8 (m, 1H).

8.2 N-(6-Hydroxy-7,8-dihydro-6H-pyrrolo[2',1':2,3]imidazo[4,5-b]pyridin-3-yl)-5-trifluoromethyl-1-(3-fluorobenzyl)-1H-indole-2-carboxamide (Compound 32)

A solution of 0.065 g (0.07 mmol) of 3-[[[1-(3-fluorobenzyl)-5-trifluoromethyl-1H-indol-2-yl]carbonyl]amino]-7,8-dihydro-6H-pyrrolo[2',1':2,3]imidazo[4,5-b]pyridin-6-yl pyridine-2-carboxylate, prepared in Example 8.1, in 10 ml of chloroform is admixed with 0.022 g (0.7 mmol) of methanol and 0.0127 g (0.07 mmol) of copper acetate. After seven hours of stirring at ambient temperature, the reaction mixture is diluted with 10 ml of dichloromethane and 10 ml of aqueous ammonia, with stirring. The organic phase is separated, washed with 10 ml of water, dried over sodium sulfate and concentrated under reduced pressure. The resulting product is subsequently purified by successive chromatography on a silica column and then on a neutral alumina column. This gives 0.012 g of the expected product.

MS: $[MH]^+$: 510

¹H NMR (DMSO D₆), δ (ppm): 8.6 (s, 1H); 8.4 (s, 1H); 8.2 (s, 1H); 7.8 (d, 1H); 7.65 (s, 1H); 7.6 (d, 1H); 7.3 (m, 1H); 7.1 (m, 1H); 6.9 (m, 2H); 6.0 (broadened peak, 2H+1H); 5.15 (m, 1H); 4.3 (m, 1H); 4.1 (m, 1H); 2.95 (m, 1H); 2.4 (m, 1H).

enantiomeric purity=92%; retention time=8.7 nm

EXAMPLE 9

Compound 33

(−)-N-(6-Dimethylamino-7,8-dihydro-6H-pyrrolo[2',1':2,3]imidazo[4,5-b]pyridin-3-yl)-5-trifluoromethyl-1-(3-fluorobenzyl)-1H-indole-2-carboxamide

9.1 5-Trifluoromethyl-1-(3-fluorobenzyl)-1H-indole-2-carboxamide

A suspension, stirred at 20° C., of 8 g (23.72 mmol) of 5-trifluoromethyl-1-(3-fluorobenzyl)-1H-indole-2-carboxylic acid (WO2006072736) in 150 ml of dry toluene is admixed with 17.3 ml (237.2 mmol) of thionyl chloride. The reaction mixture is stirred at reflux for 2 hours and then concentrated under reduced pressure. The resulting product is taken up in 25 ml of dichloromethane and this solution is poured dropwise into a solution of 9.32 ml of 30% aqueous ammonia. The reaction mixture is stirred at 20° C. for 14 hours. After this time a solid is recovered by filtration and triturated in 50 ml of pentane. Filtration and drying under reduced pressure give 5.87 g of expected product.

¹H NMR (DMSO-D₆), δ ppm: 8.28 (broadened peak, 1H); 8.13 (s, 1H); 7.77 (d, 1H); 7.6 (m, 2H); 7.41 (s, 1H); 7.32 (m, 1H); 7.05 (m, 1H); 6.9 (m, 2H); 6 (s, 2H).

9.2 (−)-N-(6-Dimethylamino-7,8-dihydro-6H-pyrrolo[2',1':2,3]imidazo[4,5-b]pyridin-3-yl)-5-trifluoromethyl-1-(3-fluorobenzyl)-1H-indole-2-carboxamide (Compound 33)

Successively, under an inert atmosphere, a pressure tube is charged with 0.4 g (1.19 mmol) of 5-trifluoromethyl-1-(3-fluorobenzyl)-1H-indole-2-carboxamide, prepared in Example 9.1, 0.068 g (0.36 mmol) of copper iodide, 0.36 g (1.31 mmol) of compound IV-h, 0.328 g (2.38 mmol) of potassium carbonate and 0.044 g (0.39 mmol) of trans-1,2-diaminocyclohexane in 10 ml of dioxane. The tube is closed and then stirred at 130° C. for 12 hours. After this time the mixture is taken up in 60 ml of a 1:1 mixture of ethyl acetate and water. The aqueous phase is separated and then washed with three times 20 ml of ethyl acetate. The organic phases are combined, washed with two times 20 ml of water, then dried over sodium sulfate and concentrated under reduced pressure. The resulting product is subsequently purified by chromatography on a silica column, eluting with a mixture of dichloromethane and methanol. This gives 87 mg of the expected product.

m.p.=203-205° C.

MS: [MH]⁺=537

[α]_D^{20}=−0.86°; c=0.558 g/100 ml (methanol)

¹H NMR (CDCl₃), δ (ppm): 9.19 (broadened peak, 1H); 8.37 (s, 1H); 8.15 (s, 1H); 7.8 (s, 1H); 7.32 (m, 2H); 7.16 (s, 1H); 7.08 (m, 1H); 6.78 (m, 2H); 6.64 (m, 1H); 5.72 (s, 2H); 4.05 (m, 2H); 3.91 (m, 1H); 2.74-2.4 (m, 2H); 2.21 (s, 6H).

EXAMPLE 10

Compound 34

N-(6-Amino-7,8-dihydro-6H-pyrrolo[2',1':2,3]imidazo[4,5-b]pyridin-3-yl)-5-fluoro-1-(3-fluorobenzyl)-1H-indole-2-carboxamide

10.1 5-Fluoro-1-(3-fluorobenzyl)-1H-indole-2-carboxamide

A suspension, stirred at 20° C., of 2 g (6.96 mmol) of 5-fluoro-1-(3-fluorobenzyl)-1H-indole-2-carboxylic acid, prepared according to the protocol described in step 1.1, in 80 ml of dry toluene is admixed with 5.08 ml (69.62 mmol) of thionyl chloride. The reaction mixture is stirred at reflux for 2 hours and then concentrated under reduced pressure. The resulting product is taken up in 10 ml of dichloromethane and this solution is poured dropwise into a solution of 9.12 ml (69.62 mmol) of 30% aqueous ammonia. The reaction mixture is stirred at 20° C. for 14 hours. After this time a solid is recovered by filtration and triturated in 50 ml of diisopropyl ether. Filtration and drying under reduced pressure give 0.58 g of expected product.

¹H NMR (DMSO-D₆), δ ppm: 8.11 (broadened peak, 1H); 7.5 (m, 3H); 7.32 (m, 1H); 7.25 (s, 1H); 7.09 (m, 2H); 6.89 (m, 2H); 5.91 (s, 2H).

10.2 N-(6-Amino-7,8-dihydro-6H-pyrrolo[2',1':2,3]imidazo[4,5-b]pyridin-3-yl)-5-fluoro-1-(3-fluorobenzyl)-1H-indole-2-carboxamide (Compound 34)

A procedure similar to Example 9.2 is carried out, starting from 0.5 g (1.75 mmol) of 5-fluoro-1-(3-fluorobenzyl)-1H-indole-2-carboxamide, described in the preceding step, and 0.659 g (1.92 mmol) of compound IV-e. This gives 208 mg of the expected product.

m.p.=218-220° C.

MS: [MH]⁺=459

¹H NMR (CDCl₃), δ (ppm): 10.61 (s, 1H); 8.6 (s, 1H); 8.4 (m, 1H); 7.6 (m, 2H); 7.5 (s, 1H); 7.3 (m, 1H); 7.2 (m, 1H); 7.1 (m, 1H); 6.9 (m, 2H); 5.9 (s, 2H); 4.45 (m, 1H); 4.25 (m, 1H); 4.0 (m, 1H); 2.9 (m, 1H); 2.3 (m, 1H).

EXAMPLE 11

Compound 35

N-(6-Acetylamino-7,8-dihydro-6H-pyrrolo[2',1':2,3]imidazo[4,5-b]pyridin-3-yl)-5-fluoro-1-(3-fluorobenzyl)-1H-indole-2-carboxamide A solution, stirred at 40° C., of 0.05 g (0.11 mmol) of compound 34, prepared in step 10.2, in 10 ml of dichloromethane is admixed with a solution of 0.013 g (0.13 mmol) of acetic anhydride in 5 ml of dichloromethane. The reaction mixture is stirred at 40° C. and then concentrated under reduced pressure. The resulting product is taken up in 10 ml of isopropyl ether, brought to boiling and then filtered while hot, and dried under reduced pressure. This gives 53 mg of the expected product.

m.p.=282-283° C.

MS: [MH]⁺=501

¹H NMR (CDCl₃), δ (ppm): 10.61 (s, 1H); 8.6 (m, 2H); 8.4 (s, 1H); 7.6 (m, 2H); 7.5 (s, 1H); 7.3 (s, 1H); 7.2 (m, 1H); 7.1

(m, 1H); 6.9 (m, 2H); 5.9 (s, 2H); 5.4 (q, 1H); 4.3 (m, 1H); 4.1 (m, 1H); 2.95 (m, 1H); 2.4 (m, 1H); 1.9 (s, 3H).

EXAMPLE 12

Compound 36

(−)-N-(6-Hydroxy-7,8-dihydro-6H-pyrrolo[2',1':2,3] imidazo[4,5-b]pyridin-3-yl)-5-trifluoromethyl-1-(3-fluorobenzyl)-1H-pyrrolo[2,3-b]pyridine-2-carboxamide 12.1 Ethyl 5-trifluoromethyl-1H-pyrrolo[2,3-b]pyridine-2-carboxylate A 100 ml round-bottomed flask equipped with a magnetic stirrer is charged with 0.3 g (1.3 mmol) of 5-trifluoromethyl-1H-pyrrolo[2,3-b]pyridine-2-carboxylic acid (*Angew Chem Int Ed* 2004, 43(34), 4526-4528) and 50 ml of ethanol. This solution is admixed with 0.5 ml of concentrated sulfuric acid. The reaction mixture is then brought to reflux for 18 hours. The cooled solution is concentrated to dryness under reduced pressure. The residue is taken up in dichloromethane (100 ml) and the organic phase is washed successively with normal aqueous sodium hydroxide solution (30 ml), with water (20 ml) and then with saturated aqueous sodium chloride solution. It is dried over sodium sulfate and then concentrated under reduced pressure. This gives 0.29 g (1.12 mmol) of the expected product in the form of a yellow powder.

$^1$H NMR (DMSO D$_6$), δ (ppm): 12.95 (s, NH); 8.8 (d, 1H); 8.6 (d, 1H); 7.3 (s, 1H); 4.4 (q, 2H); 1.35 (t, 3H).

12.2 Ethyl 5-trifluoromethyl-1-(3-fluorobenzyl)-1H-pyrrolo[2,3-b]pyridine-2-carboxylate A solution of 0.3 g (1.16 mmol) of product obtained in step 12.1, in 20 ml of dry tetrahydrofuran, maintained under inert atmosphere, is admixed successively with stirring with 0.23 g (1.74 mmol) of 3-fluorobenzyl alcohol and then 0.46 g (1.74 mmol) of triphenylphosphine. Added subsequently dropwise is 0.31 g (1.74 mmol) of diethyl azodicarboxylate. The reaction mixture is then stirred for 20 h at ambient temperature and then concentrated under reduced pressure. The resulting oil is purified by chromatography on a silica gel column, eluting with a mixture of heptane and ethyl acetate. This gives 0.34 g (0.93 mmol) of the expected product.

$^1$H NMR (DMSO D$_6$), δ (ppm): 8.9 (d, 1H); 8.7 (d, 1H); 7.5 (s, 1H); 7.4-6.95 (m, 2H); 6.85 (m, 2H); 5.9 (s, 2H); 4.3 (q, 2H), 1.3 (t, 3H).

12.3 5-Trifluoromethyl-1-(3-fluorobenzyl)-1H-pyrrolo[2,3-b]pyridine-2-carboxylic acid A solution of 3.15 g (8.6 mmol) of ethyl 5-trifluoromethyl-1-(3-fluorobenzyl)-1H-pyrrolo[2,3-b]pyridine-2-carboxylate, obtained in step 12.2, in 100 ml of ethanol and 26 ml of 2N sodium hydroxide solution is stirred at reflux for four hours. After this time the reaction mixture is concentrated under reduced pressure and then taken up in 40 ml of water. The mixture is acidified to a pH of 3 by successive additions of 1N hydrochloric acid. The precipitate is recovered by filtration, washed with water and then dried under reduced pressure. This gives 2.9 g of the expected product, in the form of a white powder, which is used as it is in the following step.

$^1$H NMR (DMSO D$_6$), δ (ppm): 13.5 (broadened peak, 1H); 8.81 (d, 1H); 8.63 (d, 1H); 7.47 (s, 1H); 7.3 (m, 1H); 7.1-6.8 (m, 3H); 5.94 (s, 2H).

12.4 (−)-N-(6-Hydroxy-7,8-dihydro-6H-pyrrolo[2',1':2,3]imidazo[4,5-b]pyridin-3-yl)-5-trifluoromethyl-1-(3-fluorobenzyl)-1H-pyrrolo[2,3-b]pyridine-2-carboxamide (Compound 36)

A procedure analogous to the method described in step 1.2 is carried out, starting from 0.3 g (0.89 mmol) of 5-trifluoromethyl-1-(3-fluorobenzyl)-1H-pyrrolo[2,3-b]pyridine-2-carboxylic acid, prepared in step 12.3, 0.25 g (1.33 mmol) of the compound IV-c, 0.19 g (0.98 mmol) of N-(3-dimethylaminopropyl)-N'-ethylcarbodiimide hydrochloride and 0.13 g (0.98 mmol) of N-1-hydroxybenzotriazole in 10 ml of dimethylformamide. This gives 0.350 g of expected product.

m.p.: 279-280° C.

MS: [MH]$^+$: 511

[α]$_D^{20}$: −3.367°; c=0.398 g/100 ml (DMSO)

$^1$H NMR (CDCl$_3$), δ (ppm): 8.8 (s, 1H); 8.7 (s, 1H); 8.5 (s, 1H); 8.4 (s, 1H); 7.6 (s, 1H); 7.3 (m, 1H); 7.1 (m, 3H); 6.0 (broadened peak, 2H+1H); 5.2 (m, 1H); 4.25 (m, 1H); 4.1 (m, 1H); 3.0 (m, 1H); 2.4 (m, 1H).

EXAMPLE 13

Compound 28

(−)-N-(6-Hydroxy-7,8-dihydro-6H-pyrrolo[2',1':2,3]imidazo[4,5-b]pyridin-3-yl)-6-trifluoromethyl-1-(3-fluorobenzyl)-1H-indole-2-carboxamide A procedure similar to the method described in step 1.2 is carried out, starting from 0.3 g (0.89 mmol) of 6-trifluoromethyl-1-(3-fluorobenzyl)-1H-indole-2-carboxylic acid (WO2006072736), 0.25 g (1.33 mmol) of the compound IV-c, 0.19 g (0.98 mmol) of N-(3-dimethylaminopropyl)-N'-ethylcarbodiimide hydrochloride and 0.13 g (0.98 mmol) of N-1-hydroxybenzotriazole in 10 ml of dimethylformamide. This gives 0.30 g of expected product.

m.p.=269-271° C.

MS: [MH]$^+$=510

[α]$_D^{20}$=−2.614°, c=0.306 g/100 ml; DMSO $^1$H NMR (CDCl$_3$), δ (ppm): 8.6 (d, 1H); 8.4 (d, 1H); 8.1 (m, 2H); 7.6 (s, 1H); 7.5 (d, 1H); 7.35 (m, 1H); 7.1 (m, 3H); 6.9 (broadened peak, 2H+1H); 6.0 (s, 2H); 5.2 (m, 1H); 4.3 (m, 1H); 4.1 (m, 1H); 2.9 (m, 1H); 2.4 (m, 1H).

It is possible to prepare compounds 37 and 38 according to a method analogous to the methods described in the above examples.

EXAMPLE 14

Compound 37

(+)-N-(6-Fluoro-7,8-dihydro-6H-pyrrolo[2',1':2,3]imidazo[4,5-b]pyridin-3-yl)-6-trifluoromethyl-1-(3-fluorobenzyl)-1H-indole-2-carboxamide

[α]$_D^{20}$=+33.10°, c=0.113 g/100 ml; MeOH $^1$H NMR (DMSO D$_6$), δ (ppm): 10.8 (s, 1H); 8.7 (s, 1H); 8.5 (s, 1H); 8.1 (s, 1H); 8 (d, 1H); 7.6 (s, 1H); 7.5 (d, 1H); 7.35 (m, 1H); 7.1 (m, 1H); 6.9 (m, 2H); 6.25-6.1 (m, 1H); 6 (s, 2H); 4.4 (m, 1H); 4.3 (m, 1H); 3.15 (m, 1H); 2.8 (m, 1H).

EXAMPLE 15

Compound 38

N-(6-Amino-7,8-dihydro-6H-pyrrolo[2',1':2,3]imidazo[4,5-b]pyridin-3-yl)-5-trifluoromethyl-1-(3-fluorobenzyl)-1H-indole-2-carboxamide $[\alpha]_D^{20}$ not determined $^1$H NMR (CDCl$_3$), δ (ppm): 9.1 (s, 1H); 8.3 (d, 1H); 8.1 (s, 1H); 7.8 (s, 1H); 7.3 (m, 2H); 7.15 (m, 1H); 6.7 (m, 4H); 5.8 (s, 2H); 4.4 (t, 1H); 4.2 (m, 1H); 3.95 (m, 1H); 2.9 (m, 1H); 2.3 (m, 1H); 2.0 (broadened peak, 2H).

Table 2 below illustrates the chemical structures and the physical properties of some examples of compounds according to the invention.

In this table:

the "configuration" column indicates, where appropriate, the value of the optical rotation of the compound, in degrees, measured at a temperature of 20° C., and also the solvent employed and the concentration in g/100 ml of the sample; or else the enantiomeric purity measured by chiral phase chromatography. "(+/−)" indicates that the compound is a racemic mixture;

the column "m.p. (° C.)" reports the melting points of the products, in degrees Celsius (° C.);

the compounds are in free base form;

"Ac" corresponds to an acetyl group; "OH" corresponds to a hydroxyl group; "Ph" corresponds to a phenyl group.

TABLE 2

(Ic)

| Compound | X$_1$, X$_2$, X$_3$, X$_4$ | R$_3$ | R'$_3$ | m | Configuration [α]$_D^{20}$ (°); g/100 ml; solvent | m.p. (° C.) |
|---|---|---|---|---|---|---|
| 1 | CH, C—F, CH, CH | H | H | 1 | — | 227-229 |
| 2 | CH, C—F, CH, CH | OAc | H | 1 | (+/−) | 139-141 |
| 3 | CH, C—F, CH, CH | OH | H | 1 | (+/−) | 288-290 |
| 4 | C—F, CH, CH, CH | H | H | 1 | — | 265-266 |
| 5 | CH, CH, CH, C—F | H | H | 1 | — | 237-239 |
| 6 | CH, CH, C—F, CH | H | H | 1 | — | 235-236 |
| 7 | CH, CH, C—CF$_3$, CH | H | H | 1 | — | 261-262 |
| 8 | CH, C—CF$_3$, CH, CH | H | H | 1 | — | 223-225 |
| 9 | C—Cl, CH, CH, CH | H | H | 1 | — | 302-303 |
| 10 | CH, CH, C—Cl, CH | H | H | 1 | — | 252-253 |
| 11 | CH, C—Cl, CH, CH | H | H | 1 | — | 263-264 |
| 12 | CH, CH, CH, CH | H | H | 1 | — | 243-244 |
| 13 | C—CH$_3$, CH, CH, CH | H | H | 1 | — | 303-304 |
| 14 | CH, CH, C—CH$_3$, CH | H | H | 1 | — | 182-183 |
| 15 | CH, C—CH$_3$, CH, CH | H | H | 1 | — | 237-238 |
| 16 | CH, CH, C—CH$_2$CH$_3$, CH | H | H | 1 | — | 224-226 |
| 17 | CH, CH, C—CH(CH$_3$)$_2$, CH | H | H | 1 | — | 275-278 |
| 18 | CH, C—C(CH$_3$)$_3$, CH, CH | H | H | 1 | — | 234-236 |
| 19 | CH, CH, C—C(CH$_3$)$_3$, CH | H | H | 1 | — | 244-245 |

TABLE 2-continued

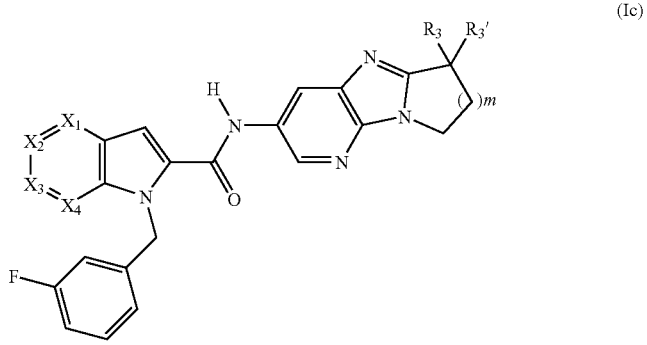

(Ic)

| Compound | $X_1, X_2, X_3, X_4$ | $R_3$ | $R'_3$ | m | Configuration $[\alpha]_D^{20}$ (°); g/100 ml; solvent | m.p. (° C.) |
|---|---|---|---|---|---|---|
| 20 | C—CH$_3$, CH, CH, C—CH$_3$ | H | H | 1 | — | 286-288 |
| 21 | CH, C—SO$_2$—CH$_3$, CH, CH | H | H | 1 | — | 275-277 |
| 22 | CH, CH, C—SCH$_3$, CH | H | H | 1 | — | 222-223 |
| 23 | CH, CH, C—CF$_3$, N | H | H | 1 | — | 272-273 |
| 24 | CH, C—CF$_3$, CH, N | H | H | 1 | — | 247-249 |
| 25 | CH, C—F, CH, N | H | H | 1 | — | 242-243 |
| 26 | CH, C—CF$_3$, CH, CH | OH | H | 1 | Enantiomeric purity = 94%; Rt = 14.5 mn* | 267-268 |
| 27 | CH, C—CF$_3$, CH, CH | H | H | 2 | — | 262-263 |
| 28 | CH, CH, C—CF$_3$, CH | OH | H | 1 | −2.614°, c = 0.306; DMSO | 269-271 |
| 29 | CH, C—CF$_3$, CH, CH | OH | H | 1 | (+/−) | 254-255 |
| 30 | CH, C—CF$_3$, CH, CH | Ph | H | 1 | (+/−) | 129-130 |
| 31 | CH, C—CF$_3$, CH, CH | Me | Me | 1 | — | 212-213 |
| 32 | CH, C—CF$_3$, CH, CH | OH | H | 1 | Enantiomeric purity = 92%; Rt = 8.7 mn* | 510* |
| 33 | CH, C—CF$_3$, CH, CH | N(CH$_3$)$_2$ | H | 1 | −0.86; c = 0.558 Methanol | 203-205 |
| 34 | CH, C—F, CH, CH | NH$_2$ | H | 1 | (+/−) | 218-220 |
| 35 | CH, C—F, CH, CH | NHAc | H | 1 | (+/−) | 282-283 |
| 36 | CH, C—CF$_3$, CH, N | OH | H | 1 | −3.367, c = 0.398 DMSO | 279-280 |
| 37 | CH, CH, C—CF$_3$, CH | F | H | 1 | +33.10°, c = 0.113; MeOH | 512** |
| 38 | CH, C—CF$_3$, CH, CH | NH$_2$ | H | 1 | not determined | 509** |

**value [MH]+ measured by mass spectrometry
*The retention times (Rt) were measured by chiral HPLC on a Chiralpak AD-H column (250* 4.6 mm; 3.5 µM) by using a solution of ethanol and of diethylamine 1000/1 as eluent, at room temperature with a flow rate of 0.8 ml/mn, detection at 220 nM, by injecting 10 µl of a solution in ethanol.

The compounds according to the invention were subjected to pharmacological tests in vitro and in vivo, which demonstrated their advantage as substances having therapeutic activities. These compounds exhibit an antagonist or agonist activity with respect to TRPV1 (or VR1) receptors.

Test for Inhibition of the Current Induced by Capsaicin on Rat DRGs

Primary Culture of Rat Dorsal Root Ganglion (DRG) Cells:

The neurons of the DRG naturally express the TRPV1 receptor.

Newborn rat DRG primary cultures are prepared from 1-day-old rat pups. Briefly, after dissection, the ganglia are trypsinized and the cells are mechanically dissociated by controlled trituration. The cells are resuspended in an Eagle's basal culture medium containing 10% of fetal calf serum, 25 mM KCl, 2 mM glutamine, 100 µg/ml gentamicin and 50 ng/ml of NGF, and then deposited onto laminin-coated glass cover slips (0.25×10$^6$ cells per cover slip) which are then placed in 12-well Corning dishes. The cells are incubated at 37° C. in a humidified atmosphere containing 5% CO$_2$ and 95% air. Cytosine β-D-arabinoside (1 µM) is added 48 h after placement in culture, in order to prevent the development of non-neuronal cells. The cover slips are transferred into the experimental chambers for the patch-clamp studies after 7-10 days of culture.

Electrophysiology:

The measuring chambers (volume 800 µl) containing the cell preparation are placed on the platform of an inverted microscope (Olympus IMT2) equipped with Hoffman optics (Modulation Contrast, New York), and observed at the magnification of 400×. The chambers are continually perfused by gravity (2.5 ml/min) by means of a solution distributing device with 8 inlets, whose sole outlet, consisting of a polyethylene tube (500 µm aperture), is placed less than 3 mm from the cell studied. The "whole cell" configuration of the patch-clamp technique was used. The borosilicate glass pipettes (resistance 5-10 Mohms) are moved close to the cell by means of a 3D piezoelectric micromanipulator (Burleigh, PC1000). The overall currents (membrane potential fixed at −60 mV) are recorded with an Axopatch 1D amplifier (Axon Instruments, Foster City, Calif.), connected to a PC controlled by Pclamp8 software (Axon Instruments). The current traces are recorded on paper and simultaneously digitized (sampling frequency 15 to 25 Hz) and acquired on the hard drive of the PC.

The application of a 300 nM solution of capsaicin causes, on the DRG cells (voltage fixed at −70 mV), an inward cationic current. In order to minimize desensitization of the receptors, a minimum period of one minute is observed between two applications of capsaicin. After a control period (stabilization of the capsaicin response alone), the compounds of the invention to be tested are applied alone at a given concentration (concentration of 10 nM or of 1 nM) for a period of 4 to 5 minutes, during which several capsaicin+compound tests are carried out (obtaining maximum inhibition). The results are expressed as percentage inhibition of the control capsaicin response.

In the case of the VR1 antagonist compounds, the percentages of inhibition of the capsaicin response (1 µM) are between 20% and 100% for the most active compounds of the invention tested at concentrations of 0.1 to 10 nM. These are therefore effective antagonists of TRPV1 receptors. Table 3 gives an example of the percentage inhibition obtained with the compounds of the invention.

TABLE 3

| Compound | % inhibition in DRG patch |
| --- | --- |
| 1 | 69% (10 nM) |

Pain Induced by Intraplantar Administration of Capsaicin in Mice

The intraplantar injection of capsaicin in mice rapidly produces a short-duration nociceptif behavior which is manifested in instances of licking, chewing and flexing of the treated paw. These nociceptive responses are probably linked to activation of the local TRPV1 receptors by the capsaicin.

Methodology:

(E)-capsaicin is initially diluted at 3 mg/ml in DMSO, then diluted again, for its final use, at 1.5 µg/20 µl in physiological saline. Administration of solvent has no effect at all on the behavior of the mouse. The capsaicin is injected into one of the hind paws of the animal, at the level of the upper face.

The compounds to be tested are administered orally 120 minutes prior to injection of capsaicin. Two hours after the administration of the compounds, the mice are placed in a glass beaker. The nociceptif behavior of the animals is then immediately evaluated by the person carrying out the experiment, and the duration of the behavioral manifestations induced by the capsaicin is recorded with a stop watch for a time of 2 minutes (licking and chewing, total or partial flexing of the injected paw).

For each compound an inhibition is determined which corresponds to the mean of the nociceptive responses induced by the capsaicin in response to a dose of test product (expressed in mg/kg) administered orally, on a sample of a specific number of mice (n). Table 4 gives an example of the percentage inhibition obtained with the compounds of the invention.

TABLE 4

| Compound | Dose | n | % inhibition of nociceptive responses induced by capsaicin |
| --- | --- | --- | --- |
| 29 | 30 mg/kg | 10 | 63% (+/−11%) |

The compounds of the invention can therefore be used for the preparation of medicaments, in particular for the preparation of a medicament for preventing or treating pathologies in which TRPV1 receptors are involved.

The compounds of the invention can be used for preventing or treating pathologies in which TRPV1 receptors are involved.

Thus, a subject of the invention provides medicaments which comprise at least one compound of formula (I), or a pharmaceutically acceptable salt, or else a hydrate or a solvate of said compound.

These medicaments find use in therapeutics, in particular in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, bites or stings, post-herpetic neuralgia, muscle pain, trapped nerves (central and/or peripheral), spinal column and/or brain trauma, ischaemia (of the spinal column and/or of the brain), neurodegeneration, hemorrhagic strokes (of the spinal column and/or of the brain) and post-stroke pain.

The compounds of the invention can also be used for preventing and/or treating metabolic disorders such as diabetes and obesity.

The compounds of the invention can also be used for preventing and/or treating urological disorders such as bladder hyperactivity, bladder hyperreflexia, bladder instability, incontinence, urgent urination, urinary incontinence, cystitis, nephritic colic, pelvic hypersensitivity and pelvic pain.

The compounds of the invention can be used for preventing and/or treating gynecological disorders such as vulvodynia and pain associated with salpingitis or with dysmenorrhea.

These products can also be used for preventing and/or treating gastrointestinal disorders such as gastroesophageal reflex disorder, stomach ulcers, duodenal ulcers, functional dyspepsia, colitis, IBS, Crohn's disease, pancreatitis, oesophagitis and biliary colic.

Similarly, the products of the present invention can be used in the prevention and/or treatment of respiratory disorders such as asthma, coughing, chronic obstructive pulmonary disease (COPD), bronchoconstriction and inflammatory disorders.

These products can also be used for preventing and/or treating psoriasis, pruritus, dermal, ocular or mucosal irritations, herpes and shingles.

The compounds of the invention can also be used for treating depression.

The compounds of the invention can also be used for treating central nervous system diseases such as multiple sclerosis, Parkinson's disease and Huntington's disease.

According to another of its aspects, the present invention relates to pharmaceutical compositions comprising, as active principle, at least one compound according to the invention. These pharmaceutical compositions contain an effective dose of at least one compound according to the invention, or a pharmaceutically acceptable salt, a hydrate or a solvate of said compound, and also at least one pharmaceutically acceptable excipient.

Said excipients are selected according to the pharmaceutical form and the desired method of administration, from the usual excipients known to the skilled person.

The pharmaceutical compositions of the present invention can be administered orally, sublingually, subcutaneously, intramuscularly, intravenously, topically, locally, intratracheally, intranasally, transdermally or rectally. These compositions can be administered in unit form, as a mixture with conventional pharmaceutical excipients. They are intended to be administered to animals and to human beings for the prophylaxis or treatment of the disorders or diseases mentioned above.

The appropriate unit administration forms include oral forms such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Said unit forms are dosed so as to allow a daily administration of from 0.001 to 30 mg of active principle per kg of body weight, depending on the specific formulation.

There may be specific cases where higher or lower dosages are appropriate; such dosages do not depart from the scope of the invention. According to the usual practice, the dosage that is appropriate for each patient is determined by the physician according to the method of administration and the weight and the response of said patient.

The compounds of the invention can also be used for the preparation of medicaments, in particular for the preparation of a medicament for use in preventing or treating pathologies in which TRPV1 receptors are involved, as mentioned above.

According to another of its aspects, the present invention also relates to a method of treating the pathologies indicated above, which comprises the administration, to a patient, of an effective dose of at least one compound according to the invention, or a pharmaceutically acceptable salt, a hydrate or a solvate thereof.

What is claimed is:
1. A compound of the formula (I):

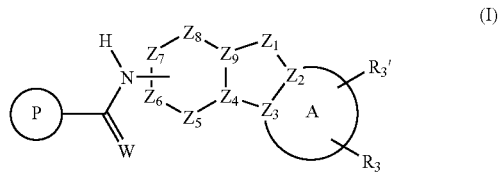

in which:
A, together with the $Z_2$—$Z_3$ bond of the bicyclic system to which it is fused, represents a $C_4$-$C_7$-cycloalkyl group, a monocyclic heteroaryl or a monocyclic heterocycle of 4 to 7 members, including from one to three heteroatoms selected from O, S and N, including the atoms $Z_2$ and $Z_3$;

$Z_1$, $Z_3$ and $Z_5$ represent a nitrogen atom;

$Z_2$, $Z_4$ and $Z_9$ represent a carbon atom;

one of $Z_6$, $Z_7$ and $Z_8$ represent a carbon atom and is bonded to the nitrogen atom of the amide or thioamide of the formula

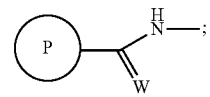

and the others of $Z_6$, $Z_7$ and $Z_8$ independently of one another are C—$R_2$;

W represents an oxygen or sulfur atom;

P represents an indolyl, pyrrolo[2,3-c]pyridinyl, pyrrolo[2,3-b]pyridinyl, pyrrolo[3,2-b]pyridinyl or pyrrolo[3,2-c]pyridinyl group as shown below, bonded at position C-2 to the carbonyl of the amide or to the thiocarbonyl of the thioamide of formula (I):

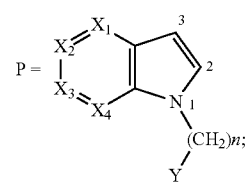

$X_1$, $X_2$, $X_3$ and $X_4$ represent, independently of one another, a nitrogen atom or a group C—$R_1$; when one of $X_1$, $X_2$, $X_3$ or $X_4$ represents a nitrogen atom, the three others represent a group C—$R_1$;

$R_1$ is selected from a hydrogen atom, a halogen atom, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryloxy-$C_1$-$C_6$-alkyl, heteroaryloxy-$C_1$-$C_6$-alkyl, aryl-$C_1$-$C_3$-alkylenoxy-$C_1$-$C_6$-alkyl, heteroaryl-$C_1$-$C_3$-alkylenoxy-$C_1$-$C_6$-alkyl, arylthio-$C_1$-$C_6$-alkyl, heteroarylthio-$C_1$-$C_6$-alkyl, aryl-$C_1$-$C_3$-alkylenethio-$C_1$-$C_6$-alkyl, heteroaryl-$C_1$-$C_3$-alkylenethio-$C_1$-$C_6$-alkyl, $C_1$-$C_6$-alkoxy, $C_3$-$C_7$-cycloalkyloxy, $C_3$-$C_7$-cycloalkyl-$C_1$-$C_3$-alkylenoxy, $C_1$-$C_6$-fluoroalkoxy, cyano, C(O)NR$_4$R$_5$, nitro, NR$_4$R$_5$, $C_1$-$C_6$-thioalkyl, $C_3$-$C_7$-cycloalkylthio, $C_3$-$C_7$-cycloalkyl-$C_1$-$C_3$-alkylenethio, —S(O)—$C_1$-$C_6$-alkyl, —S(O)—$C_3$-$C_7$-cycloalkyl, —S(O)—$C_1$-$C_3$-alkylene-$C_3$-$C_7$-cycloalkyl, $C_1$-$C_6$-alkyl-S(O)$_2$—, $C_1$-$C_6$-fluoroalkyl-S(O)$_2$—, C$_3$-C$_7$-cycloalkyl-S(O)$_2$—, C$_3$-C$_7$-cycloalkyl-C$_1$-C$_3$-alkylene-S(O)$_2$—, SO$_2$NR$_4$R$_5$, SF$_5$, NR$_6$C(O)R$_7$, NR$_6$SO$_2$R$_8$, C(O)NR$_4$R$_5$, OC(O)NR$_4$R$_5$, aryl, heteroaryl, aryl-C$_1$-C$_5$-alkylene, heteroaryl-C$_1$-C$_5$-alkylene, aryloxy, arylthio, heteroaryloxy and heteroarylthio, wherein the heteroaryl or aryl groups being optionally substituted by one or more substituents R$_9$, which are identical or different from one another;

n is 0, 1, 2 or 3;

Y represents an aryl or a heteroaryl which is optionally substituted by one or more groups selected from a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, hydroxy, C$_1$-C$_6$-alkoxy, C$_3$-C$_7$-cycloalkyloxy, C$_3$-C$_7$-cycloalkyl-C$_1$-C$_6$-alkylene-O—, C$_1$-C$_6$-fluoroalkoxy, cyano, C(O)—NR$_4$R$_5$, nitro, NR$_4$R$_5$, C$_1$-C$_6$-thioalkyl, thiol, —S(O)—C$_1$-C$_6$-alkyl, —S(O)$_2$—C$_1$-C$_6$-alkyl, SO$_2$NR$_4$R$_5$, NR$_6$C(O)R$_7$, NR$_6$SO$_2$R$_8$, C(O)NR$_4$R$_5$, OC(O)NR$_4$R$_5$, aryl-C$_1$-C$_5$-alkylene aryl, heteroaryl-C$_1$-C$_5$-alkylene and heteroaryl group, wherein the aryl and heteroaryl groups being optionally substituted by one or more substituents selected from a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylenoxy, C$_1$-C$_6$-fluoroalkoxy, nitro and cyano group;

R$_2$ represents a hydrogen atom, a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylenoxy, thiol, —S(O)—C$_1$-C$_6$-alkyl, —S(O)$_2$—C$_1$-C$_6$-alkyl, hydroxyl or C$_1$-C$_6$-fluoroalkoxy group;

R$_3$ and R$_3$' represent the substituents of A with the exclusion of the substituents of the atoms Z$_2$ and Z$_3$;

R$_3$ and R$_3$' represent, independently of one another, when they are carried by a carbon atom, a hydrogen atom, a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, hydroxyl, thiol, C$_1$-C$_6$-alkoxy, C$_3$-C$_7$-cycloalkyloxy, C$_3$-C$_7$-cycloalkyl-C$_1$-C$_3$-alkylenoxy, aryl-C(O)—O—, C$_1$-C$_6$-alkyl-C(O)—O—, C$_3$-C$_7$-cycloalkyl-C(O)—O—, C$_3$-C$_7$-cycloalkyl-C$_1$-C$_3$-alkylene-C(O)—O, C$_1$-C$_6$-fluoroalkyl-C(O)—O—, oxo, thiol, NR$_4$R$_5$, NR$_6$C(O)R$_7$, heteroaryl or aryl group, the heteroaryl and aryl groups being optionally substituted by one or more substituents selected from a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylenoxy, C$_1$-C$_6$-fluoroalkoxy, nitro and cyano group;

or else R$_3$ and R$_3$', together with the carbon atom which carries them, form a C$_3$-C$_7$-cycloalk-1,1-diyl group;

or

R$_3$ and R$_3$' represent, independently of one another, when they are carried by a nitrogen atom, a hydrogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, aryl-C(O)—, C$_1$-C$_6$-alkyl-C(O)—, C$_3$-C$_7$-cycloalkyl-C(O)—, C$_3$-C$_7$-cycloalkyl-C$_1$-C$_3$-alkylene-C(O)—, C$_1$-C$_6$-fluoroalkyl-C(O)—, aryl-S(O)—, C$_1$-C$_6$-alkyl-S(O)—, C$_1$-C$_6$-fluoroalkyl-S(O)—, C$_3$-C$_7$-cycloalkyl-S(O)—, C$_3$-C$_7$-cycloalkyl-C$_1$-C$_3$-alkylene-S(O)—, aryl-S(O)$_2$—, C$_1$-C$_6$-alkyl-S(O)$_2$—, C$_1$-C$_6$-fluoroalkyl-S(O)$_2$—, C$_3$-C$_7$-cycloalkyl-S(O)$_2$—, C$_3$-C$_7$-cycloalkyl-C$_1$-C$_3$-alkylene-S(O)$_2$—, C$_1$-C$_6$-alkyl-O—C(O)—, aryl-C$_1$-C$_3$-alkyl-O—C(O)—, C$_3$-C$_7$-cycloalkyl-O—C(O)—, C$_3$-C$_7$-cycloalkyl-C$_1$-C$_3$-alkylene-O—C(O)—, C$_1$-C$_6$-fluoroalkyl-O—C(O)—, aryl-O—C(O)—, heteroaryl-β-C(O)—, heteroaryl or aryl group, the heteroaryl and aryl groups being optionally substituted by one or more substituents selected from a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylenoxy, C$_1$-C$_6$-fluoroalkoxy, nitro and cyano group;

R$_4$ and R$_5$ represent, independently of one another, a hydrogen atom or a C$_1$-C$_6$-alkyl, C$_3$-C$_7$-cycloalkyl, C$_3$-C$_7$-cycloalkyl-C$_1$-C$_3$-alkylene, aryl-C$_1$-C$_5$-alkylene or aryl group, or R$_4$ and R$_5$, together with the nitrogen atom which carries them, form an azetidine, pyrrolidine, piperidine, azepine, morpholine, thiomorpholine, piperazine or homopiperazine group, the group NR$_4$R$_5$ being optionally substituted by a C$_1$-C$_6$-alkyl, C$_3$-C$_7$-cycloalkyl, C$_3$-C$_7$-cycloalkyl-C$_1$-C$_3$-alkylene, aryl-C$_1$-C$_6$-alkylene, aryl, heteroaryl, aryl-S(O)$_2$—, C$_1$-C$_6$-alkyl-S(O)$_2$—, C$_1$-C$_6$-fluoroalkyl-S(O)$_2$, C$_3$-C$_7$-cycloalkyl-S(O)$_2$—, C$_3$-C$_7$-cycloalkyl-C$_1$-C$_3$-alkylene-S(O)$_2$—, aryl-C(O)—, C$_1$-C$_6$-alkyl-C(O)—, C$_3$-C$_7$-cycloalkyl-C(O)—, C$_3$-C$_7$-cycloalkyl-C$_1$-C$_3$-alkylene-C(O)—, C$_1$-C$_6$-fluoroalkyl-C(O)—, hydroxy, C$_1$-C$_6$-alkyloxy, C$_3$-C$_7$-cycloalkyloxy, C$_3$-C$_7$-cycloalkyl-C$_1$-C$_3$-alkylenoxy, C$_1$-C$_6$-fluoroalkyl, aryloxy-C$_1$-C$_6$-alkylene, aryloxy, heteroaryloxy-C$_1$-C$_6$-alkylene or heteroaryloxy group;

R$_6$ and R$_7$ represent, independently of one another, a hydrogen atom, a C$_1$-C$_6$-alkyl, C$_3$-C$_7$-cycloalkyl, C$_3$-C$_7$-cycloalkyl-C$_1$-C$_3$-alkylene, aryl-C$_1$-C$_6$-alkylene or aryl group, the aryl group being optionally substituted by one or more substituents selected from a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylenoxy, C$_1$-C$_6$-fluoroalkoxy, nitro and cyano group;

or R$_6$ and R$_7$ together form a lactam of 4 to 7 members comprising the nitrogen atom and the group C(O) which carry them;

R$_8$ represents a C$_1$-C$_6$-alkyl, C$_3$-C$_7$-cycloalkyl, C$_3$-C$_7$-cycloalkyl-C$_1$-C$_3$-alkylene, aryl-C$_1$-C$_6$-alkylene or aryl group, the aryl group being optionally substituted by one or more substituents selected from a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylenoxy, C$_1$-C$_6$-fluoroalkoxy, nitro and cyano group;

or R$_6$ and R$_8$ together form a sultam of 4 to 7 members, comprising the nitrogen atom and the group S(O)$_2$ which carry them; and R$_9$ represents a halogen atom, a C$_1$-C$_6$-alkyl, C$_3$-C$_7$-cycloalkyl, C$_3$-C$_7$-cycloalkyl-C$_1$-C$_3$-alkylene, C$_1$-C$_6$-fluoroalkyl, C$_1$-C$_6$-alkoxy, C$_3$-C$_7$-cycloalkyloxy, C$_3$-C$_7$-cycloalkyl-C$_1$-C$_3$-alkylenoxy, C$_1$-C$_6$-fluoroalkoxy, nitro, cyano, NR$_4$R$_5$ or R$_4$R$_5$N—C$_1$-C$_3$-alkylene group; and wherein the sulfur atom or atoms of the heterocycle A may be in oxidized form (S(O) or S(O)$_2$);

the nitrogen atom or atoms may optionally be in oxidized form (N-oxide);

or a salt thereof.

2. The compound of formula (I) according to claim 1, wherein

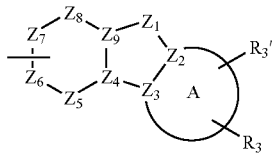

is selected from:

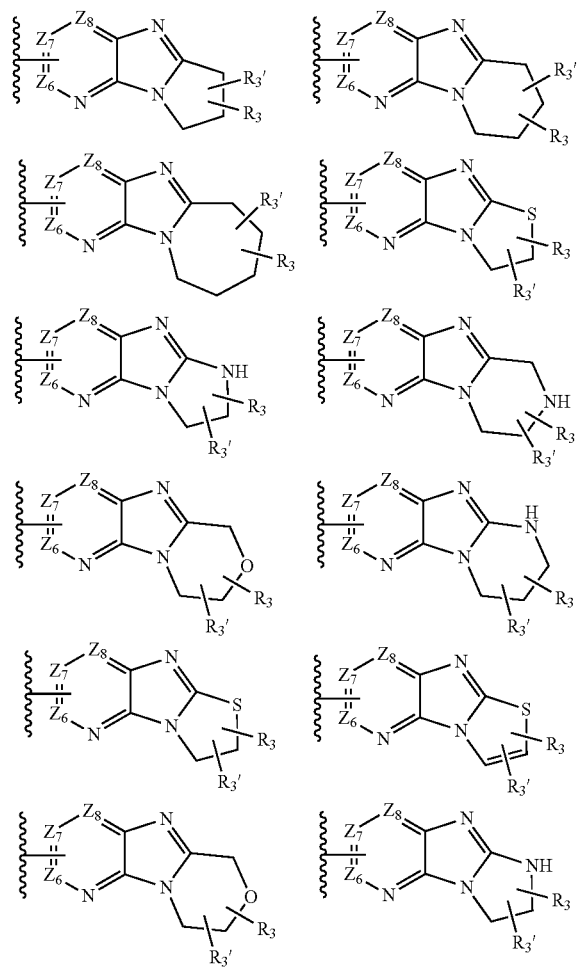

and wherein

R$_3$ and R$_3$' are as defined in claim 1.

3. The compound of formula (I) according to claim 1, wherein

R$_2$ represents a hydrogen atom;

R$_3$ and R$_3$' are carried by a carbon atom and represent, independently of one another, a hydrogen atom, a halogen atom, or a C$_1$-C$_6$-alkyl, hydroxyl, C$_1$-C$_6$-alkyl-C(O)—O—, NR$_4$R$_5$, NR$_6$C(O)R$_7$ or aryl group;

R$_4$ and R$_5$ represent, independently of one another, a hydrogen atom or a C$_1$-C$_6$-alkyl group; and R$_6$ and R$_7$ represent, independently of one another, a hydrogen atom or a C$_1$-C$_6$-alkyl group.

4. The compound of formula (I) according to claim 1, wherein

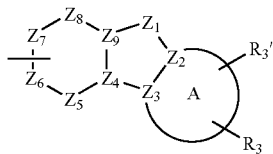

is selected from:

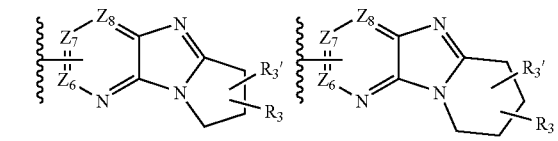

Z$_6$, Z$_7$ and Z$_8$ represent, independently of one another, a carbon atom bonded to the nitrogen atom of the amide or thioamide of formula (I), or a group C—R$_2$; wherein R$_2$ represents a hydrogen atom;

R$_3$ and R$_3$' are carried by a carbon atom and represent, independently of one another, a hydrogen atom, a halogen atom or a C$_1$-C$_6$-alkyl, hydroxyl, C$_1$-C$_6$-alkyl-C(O)—O—, NR$_4$R$_5$, NR$_6$C(O)R$_7$ or aryl group;

R$_4$ and R$_5$ represent, independently of one another, a hydrogen atom or a C$_1$-C$_6$-alkyl group; and R$_6$ and R$_7$ represent, independently of one another, a hydrogen atom or a C$_1$-C$_6$-alkyl group.

5. The compound of formula (I) according to claim 1, wherein W represents an oxygen atom.

6. The compound of formula (I) according to claim 1, wherein

P represents an indolyl or pyrrolo[2,3-b]pyridinyl group as shown below, bonded in position C-2 to the carbonyl of the amide or to the thiocarbonyl of the thioamide of formula (I):

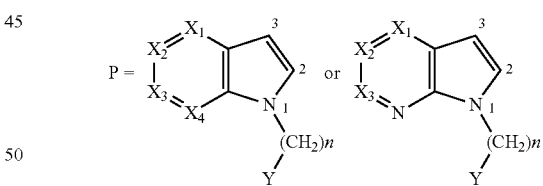

X$_1$, X$_2$, X$_3$ and X$_4$ represent, independently of one another, a group C—R$_1$; and R$_1$, Y and n are as defined in the general formula (I) according to claim 1.

7. The compound of formula (I) according to claim 1, wherein

R$_1$ is selected from a hydrogen atom, a halogen atom, C$_1$-C$_6$-alkyl, C$_1$-C$_6$-fluoroalkyl, C$_1$-C$_6$-thioalkyl and C$_1$-C$_6$-alkyl-S(O)$_2$—.

8. The compound of formula (I) according to claim 1, wherein n is 1.

9. The compound of formula (I) according to claim 1, wherein Y represents an aryl which is optionally substituted by one or more halogen atoms.

10. The compound of formula (I) according to claim 1, wherein

P represents an indolyl or pyrrolo[2,3-b]pyridinyl group as shown below, bonded in position C-2 to the carbonyl of the amide or to the thiocarbonyl of the thioamide of formula (I):

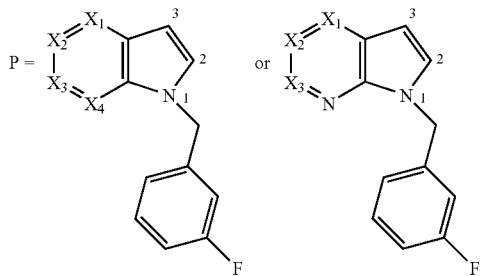

wherein $X_1$, $X_2$, $X_3$ and $X_4$ represent, independently of one another, a group C—$R_1$; and wherein $R_1$ is selected from a hydrogen atom, a halogen atom, $C_1$-$C_6$-alkyl, $C_1$-$C_6$-fluoroalkyl, $C_1$-$C_6$-thioalkyl and $C_1$-$C_6$-alkyl-S(O)$_2$—.

11. The compound of formula (I) according to claim 1, wherein

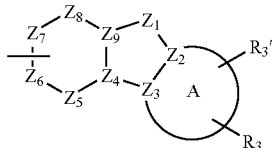

is selected from:

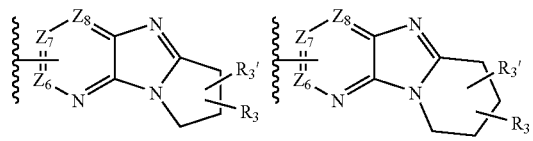

wherein $Z_6$, $Z_7$ and $Z_8$ represent, independently of one another, a carbon atom bonded to the nitrogen atom of the amide or thioamide of formula (I), or a group C—$R_2$, $R_2$ represents a hydrogen atom;

$R_3$ and $R_3'$ are carried by a carbon atom and represent, independently of one another, a hydrogen atom, a halogen atom or a $C_1$-$C_6$-alkyl, hydroxyl, $C_1$-$C_6$-alkyl-C(O)—O—, $NR_4R_6$, $NR_6C(O)R_7$ or aryl group;

$R_4$ and $R_5$ represent, independently of one another, a hydrogen atom or a $C_1$-$C_6$-alkyl group;

$R_6$ and $R_7$ represent, independently of one another, a hydrogen atom or a $C_1$-$C_6$-alkyl group;

W represents an oxygen atom;

P represents an indolyl or pyrrolo[2,3-b]pyridinyl group as shown below, bonded in position C-2 to the carbonyl of the amide of formula (I):

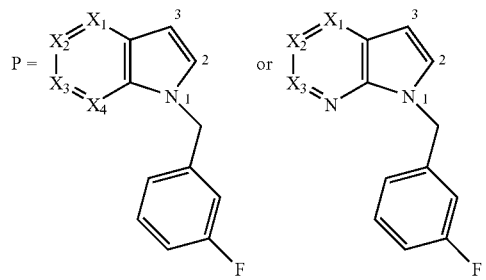

wherein $X_1$, $X_2$, $X_3$ and $X_4$ represent, independently of one another, a group C—$R_1$; and wherein $R_1$ is selected from a hydrogen atom, a halogen atom, $C_1$-$C_6$-alkyl, $C_1$-$C_6$-fluoroalkyl, $C_1$-$C_6$-thioalkyl and $C_1$-$C_6$-alkyl-S(O)$_2$—.

12. A process for preparing a compound of formula (I) according to claim 1, comprising:

reacting a compound of formula (II):

in which P and W are as defined in claim 1 with a compound of formula (III):

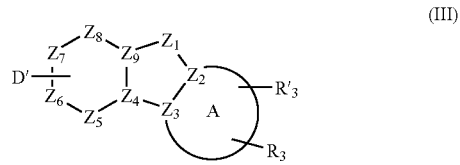

in which A, $Z_1$, $Z_2$, $Z_3$, $Z_4$, $Z_5$, $Z_6$, $Z_7$, $Z_8$, $Z_9$, $R_3$ and $R_3'$ are as defined in claim 1;

when B represents a $C_1$-$C_6$-alkoxy, $C_3$-$C_7$-cycloalkyloxy, $C_3$-$C_7$-cycloalkyl-$C_1$-$C_3$-alkylenoxy or aryl-$C_1$-$C_3$-alkylenoxy group, under reflux of a solvent, the aluminum amide of the compound of formula (III) being prepared by prior reaction of trimethylaluminum with the compound of general formula (III) in which D' represents an $NH_2$ group; or when B represents a hydroxyl group and W represents an oxygen atom, either by converting the carboxylic acid function into acid halide and then by reacting the compound of formula (II) in which B represents a chlorine atom and W represents an oxygen atom with the compound of formula (III) in which D' represents an $NH_2$ group, in the presence of a base;

or by coupling the compound of formula (II) with the compound of formula (III) in which D' represents an $NH_2$ group, in the presence of a coupling agent and a base in a solvent; or when B represents an $NH_2$ group and W represents an oxygen atom, by reacting the compound of formula (II) with the compound of formula (III) in which D' corresponds to a leaving group, in the presence of a copper salt in catalytic amount, in the presence of a catalytic amount of a ligand and in the presence of a base in a solvent.

13. A pharmaceutical composition comprising a compound of formula (I) according to claim 1 or a pharmaceutically acceptable salt thereof and at least one pharmaceutically acceptable excipient.

14. A method of treating pain in a patient comprising administering to said patient a therapeutically effective amount of a compound of formula (I) according to claim 1 or a pharmaceutically acceptable salt thereof.

* * * * *